United States Patent

Yoshino et al.

[11] Patent Number: 5,854,274
[45] Date of Patent: Dec. 29, 1998

[54] TRICYCLIC HETEROCYCLIC SULFONAMIDE AND SULFONIC ESTER DERIVATIVES

[75] Inventors: Hiroshi Yoshino, Chiba; Norihiro Ueda, Ibaraki; Jun Niijima, Ibaraki; Toru Haneda, Ibaraki; Yoshihiko Kotake, Ibaraki; Kentaro Yoshimatsu, Ibaraki; Tatsuo Watanabe, Chiba; Takeshi Nagasu, Ibaraki; Naoko Tsukahara, Chiba; Nozomu Koyanagi; Kyosuke Kitoh, both of Ibaraki, all of Japan

[73] Assignee: Eisai Co., Ltd., Tokyo, Japan

[21] Appl. No.: 760,738

[22] Filed: Dec. 5, 1996

Related U.S. Application Data

[62] Division of Ser. No. 397,254, Mar. 23, 1995.

[30] Foreign Application Priority Data

Jul. 26, 1993 [JP] Japan ................................ 5-202466
Jul. 11, 1994 [JP] Japan ................................ 6-158870

[51] Int. Cl.⁶ .................... A61K 31/44; A61K 31/40; C07D 221/06; C07D 209/82
[52] U.S. Cl. .................... 514/290; 514/411; 546/110; 546/111; 548/439; 548/440
[58] Field of Search .................... 548/439, 440; 546/110, 111; 514/411, 290

[56] References Cited

FOREIGN PATENT DOCUMENTS

| 0215200 | 3/1987 | European Pat. Off. . |
| 472053A2 | 2/1992 | European Pat. Off. . |
| 0433093 | 2/1943 | Japan . |

OTHER PUBLICATIONS

Bailey et al., Tetrahedron Letters, vol. 34, pp. 2979–2982, 1970.
Bailey et al., J. of the chemical Soc., Perkins Trans. 1, vol. 17, pp. 1809–1818, 1973.
Mahboobi et al. Arch. Pharm. (Weinheim) 327, 611–617, 1994.
R.M. Acheson, The Chemistry of Heterocyclic Compounds (1956), Ch. III, V. 9:105–147.
G.P. Ellis, The Chemistry of Hetercyclic Compounds (1987), V.9.
G.P. Ellis, The Chemistry of Heterocyclic Compounds (1992), V.47, Part 2.

(List continued on next page.)

Primary Examiner—Mukund J. Shah
Assistant Examiner—Bruck Kifle
Attorney, Agent, or Firm—Birch, Stewart, Kolasch & Birch, LLP

[57] ABSTRACT

Novel tricyclic heterocyclic sulfonamide derivatives and sulfonic ester derivatives which have excellent antitumor activity and are represented by the following general formula (I) and processes for producing the same are provided. The present sulfonamide derivatives or a sulfonic ester derivatives are represented by the following general formula (I):

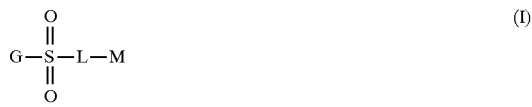

wherein G represents an aromatic 5- or 6-membered ring; L represents O or —N(R¹)— and —R¹ represents hydrogen or lower alkyl; and M represents a tricyclic structure selected from among the following;

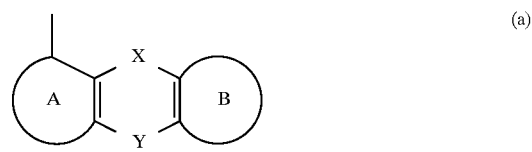

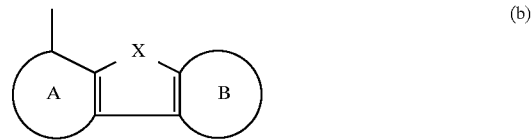

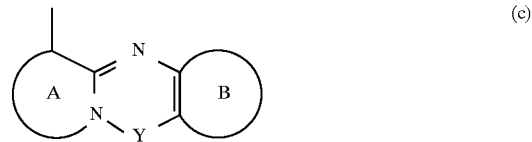

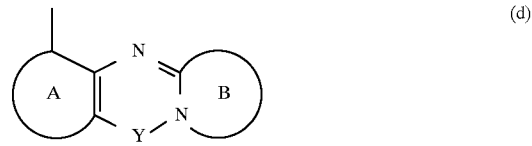

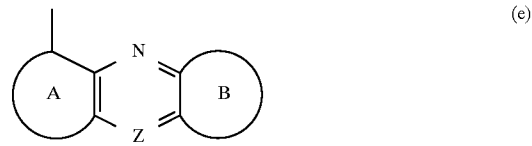

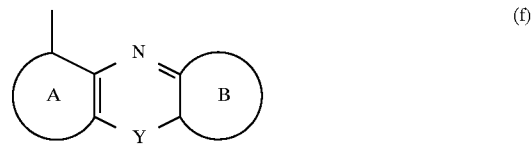

rings A and B each represent an unsaturated 5- or 5-membered ring; X represents $N(R^2)$ wherein $R^2$ represents hydrogen or lower alkyl, or NHCO; Y represents O, $S(O)_n$, $C(R^3)$ $(R^4)$, C(O), $N(R^5)$, $CH(R^6)CH(R^7)$, $C(R^8)=C(R^9)$, $N(R^{10})$ C(O), $N=CR^{11}$, $OCH(R^{12})$, $S(O)_nCH(R^{13})$ or $N(R^{14})CH(R^{15})$; Z represents nitrogen or $C(R^{16})$; and n represents 0, 1 or 2, $R^3$ to $R_{13}$, $R^{15}$ and $R^{16}$ each represent hydrogen or lower alkyl, and $R^{14}$ represents hydrogen, lower alkyl or lower acyl.

8 Claims, No Drawings

OTHER PUBLICATIONS

Capps et al., J. Med. Chem. (1992), V.35:4770–4778.
Boothroyd et al., J. Chem. Soc. (1953), Section 306, Part II, pp. 1504–1509.
Nodiff et al., J. Org. Chem. (1959), V.25:60–65.
Mital et al., J. Chem. Soc. (C) (1969), pp. 2148–2151.
Bendall et al., Aust. J. Chem. (1972), V.25:2451–2465.
Davy et al., Chemistry and Industry (1985), pp. 824–827.
Maller et al., J. of Labelled Compounds and Radiopharmaceuticals, V.XX, No. 12, pp. 1339–1349.
Abdel–Hamid, Effect of Some New Uracil Der . . . , Egypt. J. Pharm. 34 (1–3) 67, 1993.

Fathalia, Biological Activity of Some New Uracil Der . . . , Bull. Natl. Res. Cent. 18 (1) p. 55, 1993.

Shirai H., Synthesis of 1 Amino . . . , NSDYAI (18), pp. 77–78, 1970.

Chemical Abstract 122:23305, Abdel–Hamid, "Effect of Some New Uracil Der . . . ", Egypt. J. Pharm. 34 (1–3) 67 (1993).

Chemical Abstract 120:208026, Fathalia, "Biological Activity of Some New Uracil Der . . . ", Bull. Natl. Res. Cent. 18 (1) p. 55 (1993).

TRICYCLIC HETEROCYCLIC SULFONAMIDE AND SULFONIC ESTER DERIVATIVES

This application is a divisional of copending application Ser. No. 08/397,254, filed on Mar. 23, 1995, the entire contents of which are hereby incorporated by reference.

FIELD OF INDUSTRIAL APPLICATION

This invention relates to a novel sulfonamide or sulfonic ester derivative, a process for producing the same and a medicinal composition comprising this compound as an active ingredient.

PRIOR ART

There have been a number of chemotherapeutic agents used for cancer, for example, alkylating agents such as cyclophosphamide, antimetabolites such as methotrexate and fluorouracil, antibiotics such as adriamycin, mitomycin and bleomycin, vincristine and etoposide originating in plants and metal complexes such as cisplatin. However each of these agents exerts an insufficient antitumor effect. Thus there has been as urgent need to develop a novel antitumor agent.

Further, there have been reported antitumor compounds of aromatic sulfonamide type such as 4-aminobenzenesulfonamide derivatives (Japanese Patent Publication No. 3093/1968), 2-sulfanilamide-quinoxaline derivatives (Japanese Patent Laid-Open No. 426/1987) and N-(2-anilino-3-pyridyl)benzenesulfonamide amide derivatives (Japanese Patent Laid-Open No. 39256/1993). No antitumor compound of aromatic sulfonic ester type has been reported so far.

DISCLOSURE OF THE INVENTION

The present invention aims at providing novel sulfonamide derivatives and novel sulfonic ester derivatives having excellent antitumor activity and differing in the basic skeleton from the conventional antitumor compounds. It further aims at providing processes for producing these compounds and medicinal compositions comprising these compounds as an active ingredient.

In view of these aims, the present inventors have conducted extensive studies to seek excellent antitumor compounds. As a result, they have found that a novel sulfonamide derivative and a novel sulfonic ester derivative with a tricyclic structure have each an excellent antitumor activity and a low toxicity, thus completing the present invention.

Accordingly, the present invention relates to a sulfonamide derivative or a sulfonic ester derivative represented by the following general formula (I) or a pharmacologically acceptable salt thereof:

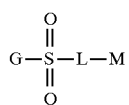
(I)

wherein

G represents an aromatic 5- or 6-membered ring having 1 or 2 substituents;

L represents —N(R$^1$)—, wherein R$^1$ represents hydrogen or lower alkyl, or oxygen; and M represents a tricyclic structure selected from among those of the following formulae (a), (b), (c), (d), (e) and (f);

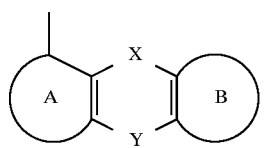
(a)

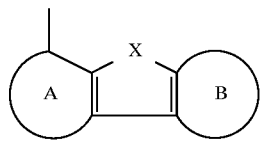
(b)

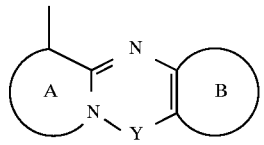
(c)

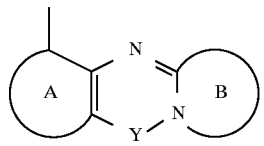
(d)

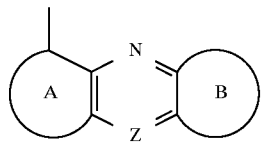
(e)

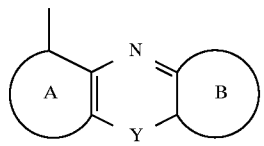
(f)

wherein rings A and B each represent an optionally substituted unsaturated 5- or 6-membered ring;

X represents —N(R$^2$)—, wherein R$^2$ represents hydrogen or lower alkyl, or —NHCO—;

Y represents oxygen, —S(O)$_n$—, —C(R$^3$)(R$^4$)—, —C(O)—, —N(R$^5$)—, —CH(R$^6$)CH(R$^7$)—, —C(R$^8$)=C(R$^9$)—, —N(R$^{10}$)C(O)—, —C(O)N(R$^{10}$)—, —N=C(R$^{11}$)—, —C(R$^{11}$)=N—, —OCH(R$^{12}$)—, —CH(R$^{12}$)O—, —S(O)$_n$CH(R$^{13}$)—, —CH(R$^{13}$)S(O)$_n$—, —N(R$^{14}$)CH(R$^{15}$)— or —CH(R$^{15}$)N(R$^{14}$)—, wherein n represents 0, 1 or 2, R$^3$, R$^4$, R$^6$, R$^7$, R$^8$ and R$^9$ are the same or different from one another and each represents hydrogen or lower alkyl, R$^5$, R$^{10}$, R$^{11}$, R$^{12}$, R$^{13}$ and R$^{15}$ each represents hydrogen or lower alkyl, and R$^{14}$ represents hydrogen, lower alkyl or lower acyl; and Z represents nitrogen or —C(R$^{16}$)=, wherein R$^{16}$ represents hydrogen or lower alkyl;

provided that a combination wherein G is 4-methylphenyl or 4-methoxycarbonylaminophenyl, X in the tricyclic structure (a) of M is —N(R$^2$)— and Y is oxygen or —S(O)$_n$—, wherein n is 0, is excluded therefrom The present invention involves the following modes.

A sulfonamide derivative or a sulfonic ester derivative represented by the following general formula (I-a) or a pharmacologically acceptable salt thereof:

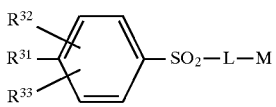

wherein

R$^{31}$ represents hydrogen, halogen, lower alkyl, lower alkoxy, nitro, cyano or amino optionally substituted by lower alkyl;

R$^{32}$ and R$^{33}$ are the same or different from each other and each represents hydrogen, lower alkyl, lower alkoxy or halogen;

L represents —N(R$^{34}$)— or oxygen, wherein R$^{34}$ represents hydrogen or lower alkyl; and M represents a tricyclic structure selected from among those of the following formulae (a), (b), (c), (d), (e) and (f):

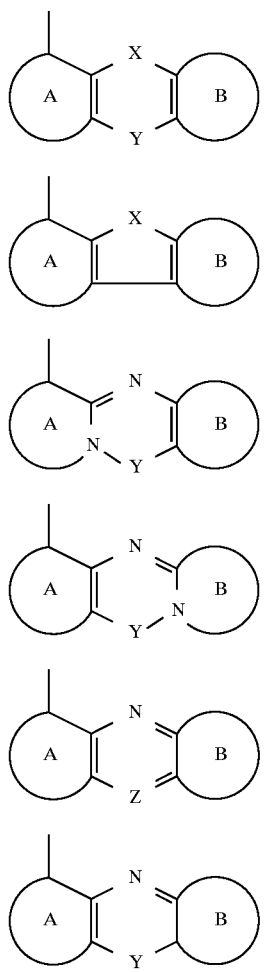

wherein rings A and B represent each an optionally substituted unsaturated 5- or 6-membered ring;

X represents —N(R$^{35}$)— or —NHCO—;

Y represents oxygen, sulfur, —S(O)—, —S(O$_2$)—, —C(R$^{36}$)(R$^{37}$)—, —C(O)—, —N(R$^{38}$)—, —CH$_2$CH$_2$—, —CH═CH—, —NHCO—, —CONH—, —CH═N—, —N═CH—, —CH$_2$O—, —OCH$_2$—, —CH$_2$S—, —SCH$_2$—, —CH$_2$N(R$^{39}$)—, —N(R$^{40}$)CH$_2$—, —CH$_2$S—(O)—, —S(O)CH$_2$—, —CH$_2$S(O$_2$)— or —S(O$_2$)CH$_2$—; and Z represents nitrogen or C-R$^{41}$;

wherein R$^{35}$, R$^{36}$, R$^{37}$, R$^{38}$, R$^{39}$ R$^{40}$ and R$^{41}$ each represents hydrogen or lower alkyl;

provided that a combination wherein R$^{31}$ is hydrogen or methyl, R$^{32}$ and R$^{33}$ are each hydrogen, L is —N(R$^{34}$)—, X in the tricyclic structure (a) of M is —N(R$^{35}$)— and Y is sulfur or oxygen is excluded therefrom.

The present invention further provides a medicinal composition comprising a pharmacologically efficacious dose of the above-mentioned sulfonamide derivative or sulfonic ester or a pharmacologically acceptable salt thereof and a pharmaceutically acceptable filler, a method of treating or preventing a tumor by administering the above-mentioned sulfonamide derivative or sulfonic ester derivative or pharmacologically acceptable salt thereof in a pharmacologically efficacious dose to a patient actually or possibly having a tumor, the use of the above-mentioned sulfonamide derivative or sulfonic ester or a pharmacologically acceptable salt thereof as a medicine for treating or preventing a tumor, and the application thereof to the production of the above-mentioned medicine.

The present invention is efficacious in the treatment or prevention of, for example, nasopharyngeal cancer, pulmonary cancer, intestinal cancer, mammary cancer, uterus cancer, gastric cancer, ovarian cancer, liver cancer and leukemia, and in the treatment or prevention of tumors of these cancers.

Now, the present invention will be described in greater detail.

The "aromatic 5- or 6-membered ring having 1 or 2 substituents" represented by G in the above general formula (I) means benzene, pyridine, thiophene or furan having 1 or 2 substituents. Examples of the substituent include halogen atoms, lower alkyl groups, lower alkoxy groups and amino groups optionally substituted by a lower alkyl group.

The rings A and B in the tricyclic structure represented by M in the above general formula (I) may be either the same or different from each other. The "optionally substituted unsaturated 5- or 6-membered ring" represented thereby means an optionally substituted unsaturated 5- or 6-membered hydrocarbon or an unsaturated heterocycle having a nitrogen, oxygen or sulfur atom as a heteroatom. Major examples of the unsaturated 5- or 6-membered ring include pyrrole, pyrazole, imidazole, thiophene, furan, benzene, pyridine, pyrimidine, pyrazine, and pyridazine.

The above-mentioned 5- or 6-membered ring may have 1 to 3 substituents. Examples of the substituent include halogen atoms, lower alkyl groups optionally substituted by a hydroxyl group, lower alkoxy groups optionally substituted by a hydroxyl group, a hydroxyl group, amino groups optionally substituted by a lower alkyl group optionally having a hydroxyl group, lower acylamino groups, a cyano group, lower acyl groups and an oxo group. When the substituent is a hydroxyl group or the substituent has a hydroxyl group therein, these hydroxyl groups may be a protected one. Examples of the protected hydroxyl group include a methoxymethyloxy group, a tetrahydropyranyloxy group, a benzyloxy group, phosphoric esters, sulfuric esters, sulfonic esters (for example, esters of p-methoxybenzenesulfonic acid or methanesulfonic acid), amino acid esters (for example, esters of glycine, alanine, leucine, tyrosine, aspartic acid, glutamic acid, lysine, arginine, proline, sarcosine, β-alanine and γ-aminobutyric acid), glycosides (for example, glucoside and glucuronide), carbamoyloxy groups optionally substituted by a lower alkyl group (for example, carbamoyloxy, methylcarbamoyloxy and dimethylcarbamoyloxy groups), lower acyloxy groups (for example, those carrying 1 to 5 carbon atoms such as formyloxy, acetoxy, propionyloxy and pivaloyloxy groups) and a benzoyloxy group.

In the definition of the substituents optionally carried by $R^1$ to $R^{16}$, G and the rings A and B in the above general formula (I), the term "lower alkyl" means linear or branched alkyl groups having from 1 to 6 carbon atoms such as methyl, ethyl, n-propyl, isopropyl, n-butyl, isobutyl, sec-butyl, tert-butyl, n-pentyl (amyl), isopentyl, neopentyl, tert-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl groups. Among these groups, methyl, ethyl, propyl and isopropyl groups may be cited as preferable ones and, in particular, methyl and ethyl groups may be cited as the most desirable ones.

In the definition of the substituents optionally carried by G and the rings A and B, the term "lower alkoxy" means those derived from the above-mentioned lower alkyls, for example, methoxy, ethoxy, n-propoxy, isopropoxy, n-butoxy, isobutoxy and tert-butoxy groups. Among these groups, methoxy and ethoxy groups may be cited as preferable ones. As the halogen, fluorine, chlorine and bromine atoms may be cited.

In the definition of the substituents optionally carried by $R^{14}$ and the rings A and B, the term "lower acyl" means, for example, formyl, acetyl, propionyl, butyryl, isobutyryl and valeryl groups.

In some cases, the sulfonamide derivative or sulfonic ester derivative represented by the above general formula (I) forms a salt together with an acid or a base. These salts of the compound (I) also fall within the scope of the present invention. Examples of the salt with an acid include salts with inorganic acids such as hydrochloric, hydrobromic and sulfuric acids and those with organic acids such as acetic, lactic, succinic, fumaric, maleic, citric, benzoic, methanesulfonic and p-toluenesulfonic acids. Examples of the salt with a base include inorganic salts such as sodium, potassium and calcium salts and salts with organic bases such as triethylamine, arginine and lysine.

It is needless to say that all of the hydrates of these compounds and optical isomers thereof, if any, also fall within the scope of the present invention. The compounds of the present invention exhibit a potent antitumor activity and those which exhibit an antitumor activity after being metabolized (i.e., oxidized, reduced, hydrolyzed, conjugated, etc.) in vivo are also included in the scope of the present invention. Further, compounds which are metabolized in vivo and thus form the compounds of the present invention are included in the scope of the present invention.

The compounds (I) of the present invention can be produced by various methods. Typical examples of these methods are as follows.

(1) A sulfonic acid represented by the following general formula (II):

Gb—SO$_3$H  (II)

wherein

Gb represents optionally protected G; or a reactive derivative thereof is reacted with a compound represented by the following general formula (III)

H—L—Ma  (III)

wherein

L has the same meaning as the one defined above; and

Ma represents optionally protected M.

when the compound thus obtained has a protecting group, it may be removed, if desired. Thus the target compound can be obtained.

Examples of the reactive derivative of the sulfonic acid (II) include those commonly employed in the art, for example, sulfonyl halides, sulfonic anhydride and N-sulfonylimidazolides may be cited. As particularly preferable examples thereof, sulfonyl halides may be cited. This reaction proceeds at the stoichiometrically equimolar ratio. Although the solvent to be used in the reaction is not particularly restricted, it is desirable to use a solvent in which the starting compounds are soluble and which would not easily react with them. For example, pyridine, tetrahydrofuran, dioxane, benzene, ether, dichloromethane, dimethylformamide, or a mixture of two or more solvents selected therefrom may be employed as the solvent. In such a case as the one with the use of a sulfonyl halide where an acid is liberated with the progress of the reaction, it is preferable to effect the reaction in the presence of an appropriate deacidifying agent. In such a case, it is particularly suitable to use a basic solvent such as pyridine. When a neutral solvent is employed, a basic substance (for example, an alkali carbonate or an organic tertiary amine) may be added. As a matter of course, the solvents usable in this reaction are not restricted to those cited above. Although this reaction generally proceeds at room temperature, the reaction system may be cooled or heated, if necessary. The reaction time usually ranges from 10 minutes to 20 hours, though it can be arbitrarily selected depending on the employed starting compounds and the reaction temperature.

When the product thus obtained has a protected amino or hydroxyl group, the protecting group may be removed by a conventional method such as a treatment with an acid or a base or catalytic reduction, if desired. Thus a sulfonamide derivative or a sulfonic ester derivative (I) having a free hydroxyl or amino group can be obtained.

(2) A compound represented by the following general formula (VII):

wherein

Gb and Ma have each the same meaning as the one defined above;

is reacted with a lower alkyl halide in the presence of a base such as sodium hydride to thereby give the target compound. When the product thus obtained has a protected amino or hydroxyl group, the protecting group may be removed by a conventional method such as a treatment with an acid or a base or catalytic reduction, if desired. Thus a sulfonamide derivative (I) having a free hydroxyl or amino group can be obtained.

(3) A compound represented by the following general formula (VIII):

wherein

Gb and L have each the same meaning as the one defined above; and

Mb represents Ma as defined above wherein Y contains a sulfur atom;

is reacted with an oxidizing agent such as hydrogen peroxide or m-chloroperbenzoic acid to thereby give the target compound. When the product thus obtained has a protected amino or hydroxyl group, the protecting group may be removed by a conventional method such as a treatment with an acid or a base or catalytic reduction, if desired. Thus a sulfonamide derivative or a sulfonic ester derivative (I) having a free hydroxyl or amino group can be obtained.

(4) A compound represented by the following general formula (IV):

$$Gb-SO_2-N(R^1)-\text{[Aa ring fused to Ba ring with N and NH-R^{14a}]}-R^2 \quad (IV)$$

wherein

Gb, $R^1$ and $R^2$ have each the same meaning as the one defined above;

$R^{14a}$ represents hydrogen or lower alkyl; and rings Aa and Ba represent respectively the rings A and B which are optionally protected;

is reacted with an aldehyde such as paraformaldehyde or acetaldehyde in the presence of an acid such as hydrochloric acid or hydrobromic acid to thereby give the target compound. Although the solvent to be used in this reaction is not particularly restricted, tetrahydrofuran, methanol, water or a mixture thereof may be used therefor. The reaction temperature can be arbitrarily selected depending on the starting compounds and the reaction system may be heated, if necessary. When the product thus obtained has a protected amino or hydroxyl group, the protecting group may be removed by a conventional method such as a treatment with an acid or a base or catalytic reduction, if desired. Thus a sulfonamide derivative (I) having a free hydroxyl or amino group can be obtained.

(5) A compound represented by the following general formula (IVa):

$$Gb-SO_2-N(R^1)-\text{[Aa ring fused to Ba ring with N and NH-R^{14b}]}-R^{2a} \quad (IVa)$$

wherein

Gb, $R^1$ and rings Aa and Ba have each the same meaning as the one defined above;

$R^{2a}$ represents lower alkyl or a protecting group; and $R^{14b}$ represents lower acyl;

is reacted in the presence of, for example polyphosphoric acid or phosphorus oxychloride to thereby give the target compound. The reaction temperature can be arbitrarily selected depending on the starting compounds and the reaction system may be heated, if necessary. When the product thus obtained has a protected amino or hydroxyl group, the protecting group may be removed by a conventional method such as a treatment with an acid or a base or catalytic reduction, if desired. Thus a sulfonamide derivative (I) having a free hydroxyl or amino group can be obtained.

(6) A compound represented by the following general formula (IX):

$$Gb-SO_2-N(R^1)-\text{[Aa ring fused to Ba ring with N-R^2 and NH-R^{10}, J]} \quad (IX)$$

wherein

Gb, $R^1$, $R^2$, $R^{10}$ and rings Aa and Ba have each the same meaning as the one defined above; and J represents carboxyl or a reactive derivative thereof; is subjected to intramolecular ring closure to thereby give the target compound. The reaction temperature can be arbitrarily selected depending on the starting compounds and the reaction system may be cooled or heated, if necessary. Examples of the reactive derivative of carboxyl include esters, active esters, acid halides, acid anhydrides and active amide compounds. When the carboxyl group is to be used as such, the reaction can be effected in the presence of a condensing agent such as 1,3-dicyclohexylcarbodiimide (DCC) or diphenylphosphoryl azide (DPPA). When the product thus obtained has a protected amino or hydroxyl group, the protecting group may be removed by a conventional method such as a treatment with an acid or a base or catalytic reduction, if desired. Thus a sulfonamide derivative (I) having a free hydroxyl or amino group can be obtained.

(7) A compound represented by the following general formula (V):

$$Gb-SO_2-N(R^1)-\text{[Aa ring fused to Ba ring with N-R^2 and NHCH-R^{14}, R^{15}, V]} \quad (V)$$

wherein

Gb, $R^1$, $R^2$, $R^{14}$, $R^{15}$ and rings Aa and Ba have each the same meaning as the one defined above; and V represents a leaving group;

is subjected to intramolecular ring closure to thereby give the target compound. Examples of the leaving group V include halogen atoms and methanesulfonylxoy and p-toluenesulfonyloxy groups. It is not always necessary that the starting compound (V) be one which can be isolated. Namely, it may be temporarily formed as, for example, a reaction intermediate. When the product thus obtained has a protected amino or hydroxyl group, the protecting group may be removed by a conventional method, if desired. Thus a sulfonamide derivative (I) having a free hydroxyl or amino group can be obtained.

(7) A compound represented by the following general formula (VI):

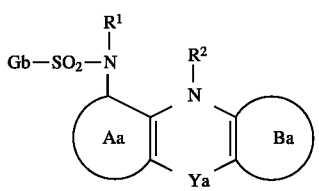

(VI)

wherein
- Gb, $R^1$, $R^2$ and rings Aa and Ba have each the same meaning as the one defined above; and
- Ya represents NHCO— or —N═C($R^{11}$), wherein $R^{11}$ has the same meaning as the one defined above; is reduced to thereby give the target compound. The reduction may be performed by a method arbitrarily selected depending on the starting compound. For example, catalytic reduction or reduction with the use of a metal hydride such as lithium aluminum hydride may be cited therefor. When the product thus obtained has a protected amino or hydroxyl group, the protecting group may be removed by a conventional method, if desired. Thus a sulfonamide derivative (I) having a free hydroxyl or amino group can be obtained.

Now, processes for producing the starting compounds to be used in the present invention will be illustrated.

The starting compound H—L—Ma (III) includes known compounds and novel ones. When H—L— in the starting compound (III) represents an amino group ($H_2N$—), $H_2N$—Ma (III) can be obtained by reducing the nitro compound $O_2N$—Ma by a method commonly employed for reducing a nitro group. Preferable examples of the reduction method include catalytic reduction with the use of palladium-carbon as the catalyst and reduction with zinc dust-acetic acid. The catalytic reduction can be effected usually in an organic solvent such as methanol, tetrahydrofuran or dimethylformamide under atmospheric or elevated pressure.

When H—L— in the starting compound (III) represents a hydroxyl group, HO—Ma (III) can be obtained through the diazotization of the above-mentioned $H_2N$—Ma followed by hydrolysis.

Alternatively, the starting compound (III) can be obtained by removing the protecting group Q in a compound represented by the following general formula (X):

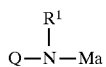

(X)

wherein
- $R^1$ and Ma have each the same meaning as the one defined above; and
- Q represents a protecting group for the amino group;

by an appropriate method. Examples of the protecting group for the amino group include benzyloxycarbonyl, acetyl, tert-butoxycarbonyl and trityl groups. The method for removing the protecting group varies depending on the type of this group. For example, catalytic reduction, a treatment with an acid or a treatment with an alkali may be employed therefor.

Next, methods for producing the nitro compound $O_2N$—Ma and Q—N($R^1$)—Ma (X), from which the starting compound (III) is produced, will be illustrated. Also, these compounds can be produced by referring to, for example, synthesis examples of various tricyclic compounds described in The Chemistry of Heterocyclic Compounds, Vol. 9, Vol. 47 and Vol. 47, Part 2.

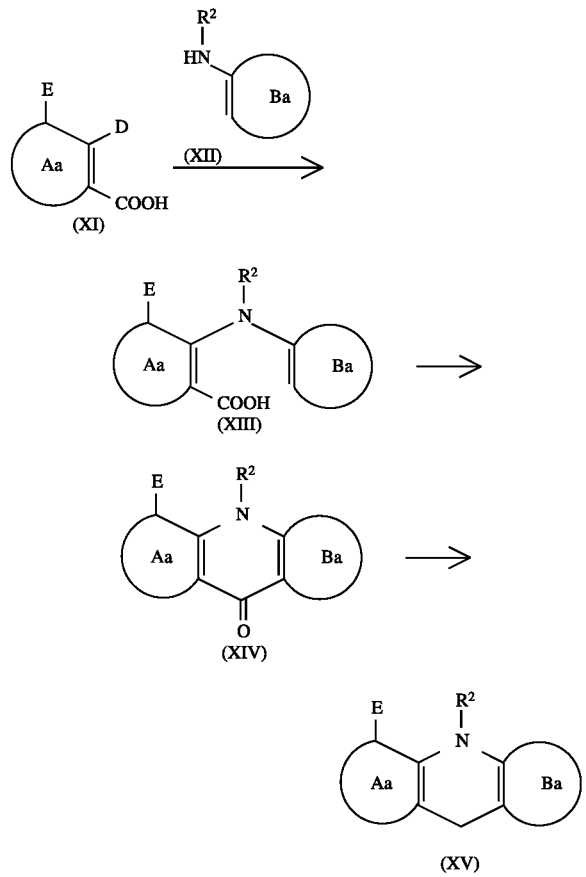

wherein
- rings Aa and Ba and $R^2$ have each the same meaning as the one defined above;
- E represents nitro or protected amino; and
- D represents a leaving group such as halogen or nitro.

The compound represented by the general formula (XIV) can be produced by methods described in various publications, for example, the method described in J. Med. Chem., 35, 4770 or a method similar thereto. Specifically, the compound represented by the general formula (XI) is heated together with the amine (XII) in N,N-dimethylaniline employed as a solvent in the presence or absence of N,N-diisopropylethylamine. The thus obtained compound (XIII) is then subjected to ring closure by reacting with phosphorus oxychloride in a solvent such as 1,2-dichloroethane in the presence of N,N-dimethylaniline under heating or by heating in conc. sulfuric acid. Thus the target compound can be synthesized.

Similarly, the compound represented by the general formula (XIV) can be synthesized via the following route too.

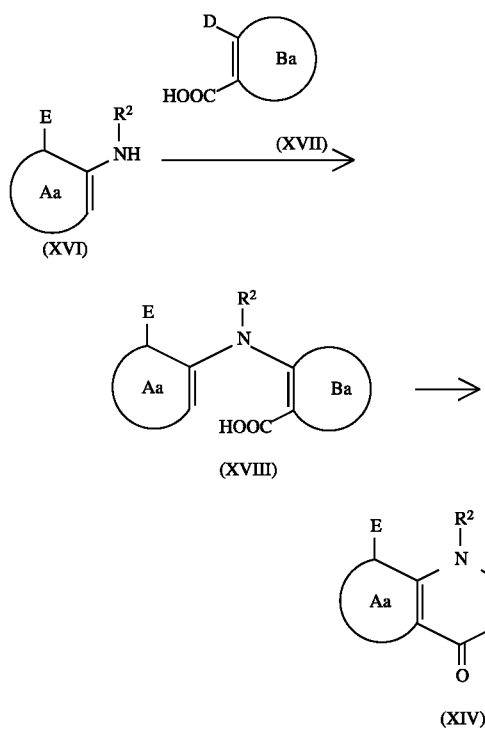

wherein
   rings Aa and Ba, $R^2$, E and D have each the same meaning as the one defined above.

The compound (XV) can be produced by reacting the compound (XIV) with a reducing agent such as lithium aluminum hydride-aluminum chloride.

Production process 2:

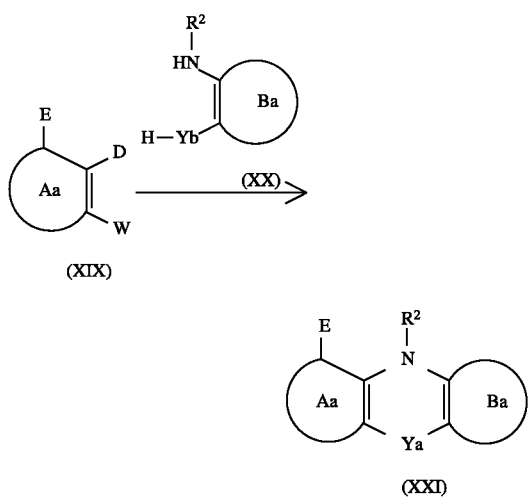

wherein
   rings Aa and Ba, $R^2$, D and E have each the same meaning as the one defined above;
   W represents a leaving group such as halogen or nitro; and Yb represents oxygen, sulfur, —N($R^5$)—, —OCH($R^{12}$)—, —SCH($R^{13}$)— or —N($R^{14}$)CH($R^{15}$)—, wherein $R^5$, $R^{12}$, $R^{13}$, $R^{14}$ and $R^{15}$ have each the same meaning as the one defined above.

The compound represented by the general formula (XXI) can be produced by methods described in various publication, for example, those described in J. Chem. Soc., (1953) 1504; J. Org. Chem., 25, 60; and J. Chem. Soc. (C), (1969), 2148 or a method similar thereto. Specifically, it can be synthesized by heating the compound represented by the general formula (XIX) and the compound represented by the general formula (XX) or its N-formyl derivative in dimethylformamide in the presence of potassium carbonate and a catalytic amount of a copper powder. Alternatively, it can be synthesized by first reacting the compound represented by the general formula (XIX) with the compound represented by the general formula (XX) in the presence or absence of sodium acetate or triethylamine at room temperature or under heating, then adding, for example, potassium carbonate or caustic soda thereto and reacting the mixture in the presence or absence of a copper powder at room temperature or under heating.

Production process 3:

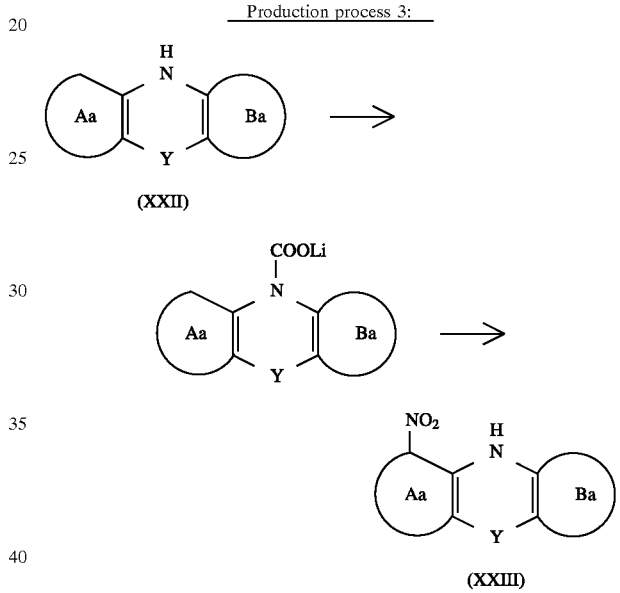

wherein
   rings Aa and Ba and Y have each the same meaning as the one defined above.

The compound represented by the general formula (XXIII) can be synthesized by, for example, the method described in Synthesis, 215(1988) or a method similar thereto. Namely, the compound represented by the general formula (XXII) is reacted with n-butyllithium in a solvent such as tetrahydrofuran. After blowing carbon dioxide thereinto, the reaction product is reacted successively with n-butyllithium and isobutyl nitrate. Thus the compound represented by the general formula (XXIII) can be synthesized.

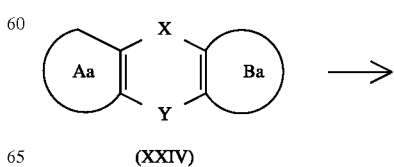

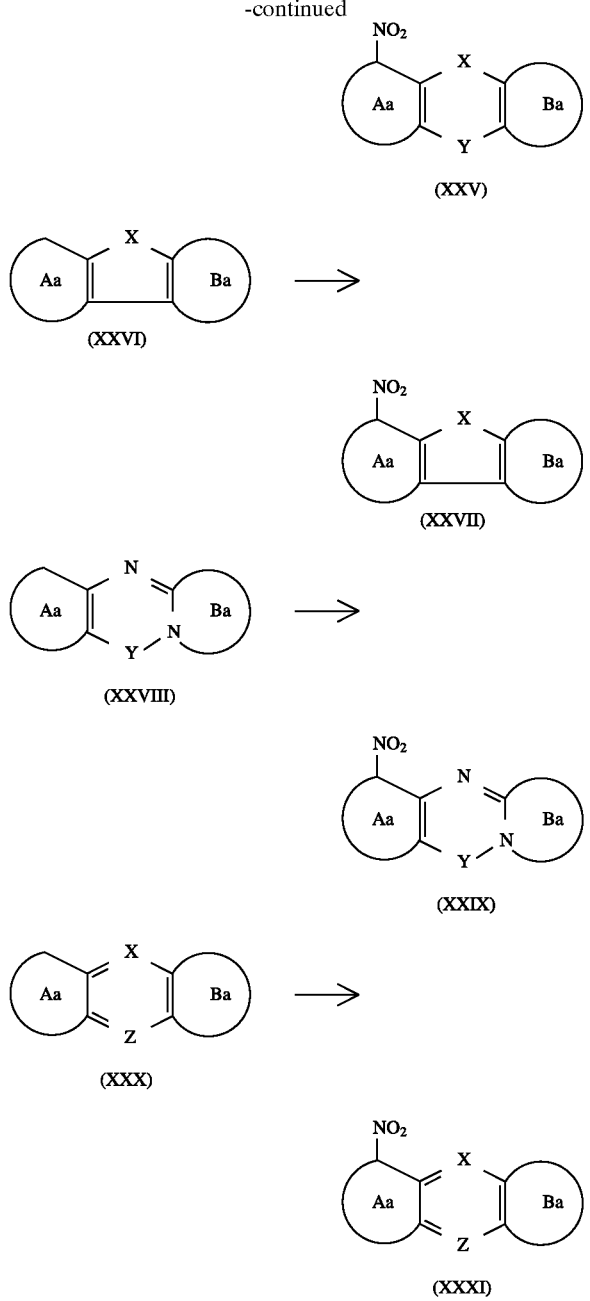

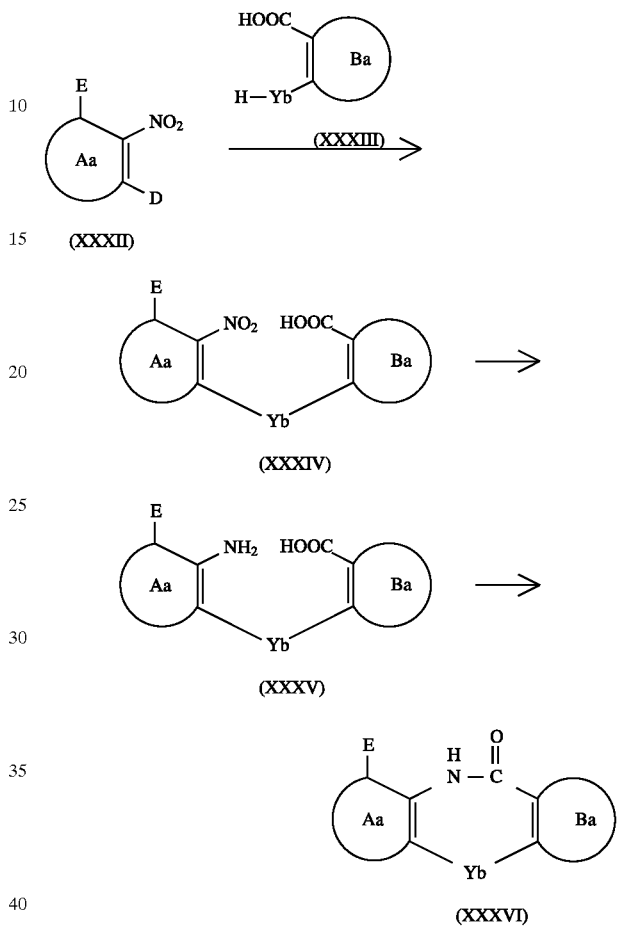

wherein
rings Aa and Ba, X, Y and Z have each the same meaning as the one defined above.

The compounds represented by the general formulae (XXV), (XXVII), (XXIX) and (XXXI) can be synthesized respectively through the nitration of the compounds (XXIV), (XXVI), (XXVIII) and (XXX) each by a conventional method with the use of a nitrating agent commonly employed in the art, for example, conc. nitric acid, fuming nitric acid, mixed acid or acetyl nitrate. In the case of the compound (XXIVa), i.e., the one of the general formula (XXIV) wherein X represents NH, the corresponding nitro compound can be synthesized by the method described in Aust. J. Chem., 25, 2451 or a method similar thereto, i.e., through the N-nitrosation of the compound (XXIVa) with nitrous acid followed by light irradiation in the presence of oxygen.

wherein
rings Aa and Ba, E, D and Yb have each the same meaning as the one defined above.

The compound represented by the general formula (XXXVI) can be produced by the method described in Chem. Ind., 825(1985) or a method similar thereto. Specifically, the compound represented by the general formula (XXXII) and the compound (XXXIII) are heated in a solvent such as dimethylformamide or ethanol in the presence of, for example, potassium carbonate and a copper powder or potassium iodide. Then the compound (XXXIV) thus obtained is reduced by a method commonly employed for reducing a nitro group. The obtained amine (XXXV) is then heated or treated with a condensing agent such as 1,3-dicyclohexylcarbodiimide. Thus the compound (XXXVI) can be synthesized.

Also, the compound represented by the general formula (XXXVI) can be produced via the following route, wherein an amide bond is first formed followed by ring closure, as described in, for example, J. Labelled Compd. Radiopharm., 20, 1399.

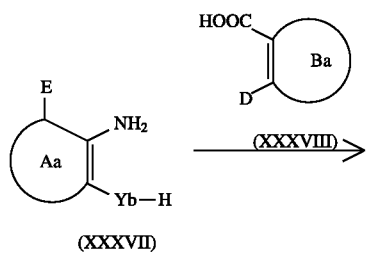

(XXXVII)

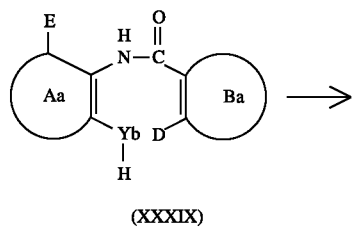

(XXXIX)

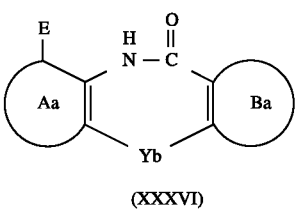

(XXXVI)

wherein rings Aa and Ba, E, D and Yb have each the same meaning as the one defined above.

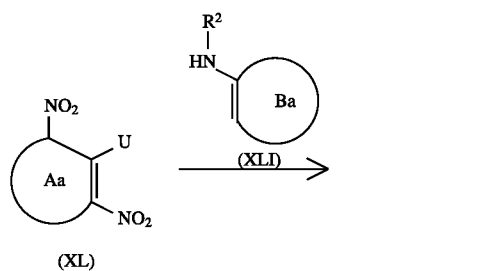

(XL)

(XLII)

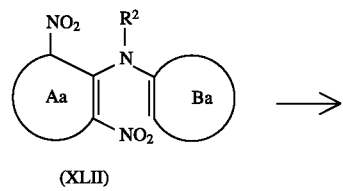

(XLIII)

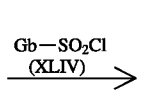

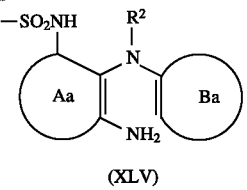

(XLV)

wherein rings Aa and Ba, $R^2$ and Gb have each the same meaning as the one defined above; and U represents a leaving group.

The compound represented by the general formula (XLV) can be synthesized from the dinitrohalide (XI) through a reaction with the amine (XLI), reduction and another reaction with the sulfonyl chloride (XLIV).

When the compound of the present invention is to be used as a medicine, it can be orally or parenterally administered. Although the dose of the compound is not particularly restricted, but varies depending on the severity of the conditions, the age, sex, body weight and sensitivity of the patient, the route, period and interval of the administration, and the properties, compounding, type and active ingredients of the medicinal preparation, it may be administered to an adult in a daily dose of from 10 to 6,000 mg, preferably from about 50 to 4,000 mg and still preferably from 100 to 3,000 mg, usually once to thrice a day.

To prepare a solid preparation for oral administration, the principal agent is blended with fillers optionally together with binders, disintegrators, lubricants, coloring agents, corrigents, etc. Then the obtained blend is formed into, for example, tablets, coated tablets, granules, fine subtilaes, dusts or capsules by a conventional method.

Usable fillers are, for example, lactose, corn starch, sucrose, glucose, sorbitol, crystalline cellulose and silicon dioxide. Usable binders are, for example, polyvinyl alcohol, ethylcellulose, methylcellulose, acacia, hydroxypropylcellulose and hydroxypropylmethylcellulose. Usable lubricants are, for example, magnesium stearate, talc and silica. Usable coloring agents are those authorized as medicinal additives. Usable corrigents are, for example, cocoa powder, menthol, aromatic powder, mentha oil, borneol and powdered cinnamon bark. As a matter of course, these tablets and granules may be coated with sugar, gelatin, etc., if desired.

To prepare an injection, the principal agent is blended optionally with pH regulators, buffer agents, suspending agents, solubilizing agents, stabilizers, tonicity agents, preservatives, etc. Then the obtained blend is formed into intravenous, subcutaneous or intramuscular injections by a conventional method. If necessary, it may be formed into a freeze-dried preparation in a conventional manner.

Examples of the suspending agents include methylcellulose, polysorbate 80, hydroxyethylcellulose, acacia, powdered tragacanth, carboxymethylcellulose sodium and polyoxyethylenesorbitan monolaurate.

Examples of the solubilizing agents include polyoxyethylene hardened castor oil, polysorbate 80, nicotinamide, polyoxyethylenesorbitan monolaurate, Macrogol and castor oil fatty acid ethyl ester.

As the stabilizers, for example, sodium sulfite and sodium metasulfite are usable. Examples of the preservatives include methyl parahydroxybenzoate, ethyl parahydroxybenzoate, sorbic acid, phenol, cresol and chlorocresol.

To illustrate the effects of the compounds of the present invention, the following pharmacological experiment examples will be given.

EXPERIMENTAL EXAMPLE 1 in vitro Antitumor test on KB cells (human nasopharyngeal cancer cells)

KB cells suspended in an RPMI1640 medium (mfd. by Nissui Seiyaku K.K.), which contained 10% of fetal calf serum, 100 U/ml of penicillin, 100 μg/ml of streptomycin, $5 \times 10^{-5}$ M of mercaptoethanol and 1 mM of sodium pyruvate, were inoculated in $1.25 \times 10^3$ portions (0.1 ml) into wells of a 96-well flat-bottomed microplate and then incubated in an incubator containing 5% of carbon dioxide at 37° C. for a day.

A compound of the present invention was dissolved in dimethyl sulfoxide in a concentration of 20 mg/ml and diluted with a 10% fetal calf serum-RPMI1640 culture medium to a concentration of 100 μg/ml. By using this concentration as the highest level, threefold serial dilution was performed with a 10% fetal calf serum-RPMI1640 culture medium. Then it was added in 0.1 ml portions into the wells of the above-mentioned plate wherein the KB cells had been incubated followed by incubation in the incubator containing 5% of carbon dioxide at 37° C. for 3 days.

After incubating, an MTT (3-(4,5-dimethylthiazol-2-yl)-2,5-diphenyltetrazolium bromide) solution (3.3 mg/ml) was added in 0.05 ml portions into the wells and the incubation was effected for additional 1 hour. After sucking off the supernatant from each well, the formazane thus formed was dissolved in 0.1 ml of dimethyl sulfoxide. Then the absorbance at 540 nm was measured with a microplate reader and employed as an indication of the vital cell count. In accordance with the following equation, the inhibitory ratio was calculated and the 50% inhibitory concentration ($IC_{50}$) of the test compound was determined.

$$\text{Inhibitory ratio (\%)} = \frac{C - T}{C} \times 100$$

T: absorbance of a well containing the test compound.
C: absorbance of a well containing no test compound.
Table 1 shows the $IC_{50}$ data thus obtained.

TABLE 1 in vitro Antitumor test on KB Cells

| Compd. (Exp. Ex. no.) | $IC_{50}$ (μg/ml) |
|---|---|
| 1 | 0.11 |
| 2 | 0.10 |
| 4 | 0.17 |
| 5 | 0.08 |
| 6 | 0.09 |
| 9 | 0.23 |
| 12 | 0.25 |
| 14 | 0.026 |
| 15 | 0.15 |
| 16 | 0.022 |
| 17 | 0.03 |
| 20 | 0.11 |
| 22 | 0.17 |
| 24 | 0.0061 |
| 25 | 0.016 |
| 26 | 0.15 |
| 28 | 0.069 |
| 29 | 0.11 |
| 30 | 0.028 |
| 31 | 0.27 |
| 32 | 0.082 |
| 33 | 0.043 |
| 34 | 0.25 |
| 35 | 0.25 |
| 38 | 0.047 |

TABLE 1-continued in vitro Antitumor test on KB Cells

| Compd. (Exp. Ex. no.) | $IC_{50}$ (μg/ml) |
|---|---|
| 39 | 0.26 |
| 40 | 0.032 |
| 41 | 0.28 |
| 42 | 0.13 |
| 43 | 0.22 |
| 44 | 0.077 |
| 45 | 0.016 |
| 46 | 0.25 |
| 47 | 0.078 |
| 48 | 0.028 |
| 49 | 0.08 |

EXPERMINTAL EXAMPLE 2 in vivo antitumor test on M5076 (mouse reticulum cell sarcoma)

$1 \times 10^6$ M5076 cells were subcutaneously transplanted into the lateral parts of $BDF_1$ mice (aged 6 to 9 weeks, female). A compound of the present invention was suspended in physiological saline containing 3.5% of dimethyl sulfoxide and 6.5% of Tween 80 and a given amount of the obtained suspension was intraperitoneally administered to the animals 4 times from the 10th day after the transplantation once a day every other day. The control group comprised 10 to 12 animals, while the test group comprised 5 or 6 animals.

On the 21st day after the transplantation, tumors were taken out and weighed. Then the tumor multiplication inhibitory ratio of each test group based on the control group was determined in accordance with the following equation.

$$\text{Multiplication inhibitory ratio (\%)} = \frac{C - T}{C} \times 100$$

T: average tumor weight of the test group.
C: average tumor weight of the control group.
Table 2 shows the results thus obtained.

TABLE 2 in vivo Antitumor test on M5076

| Compd. (Exp. Ex. no.) | Dose (mg/kg/day) | Inhibitory ratio (%) | Survival ratio on 21st day (%) |
|---|---|---|---|
| 1 | 50 | 73 | 100 |
| 17 | 100 | 81 | 100 |
| 28 | 50 | 82 | 100 |
| 30 | 100 | 82 | 100 |
| 32 | 25 | 84 | 100 |

As the above experimental examples show, the compounds of the present invention have each an excellant antitumor effect and is highly useful as an antitumor agent.

EXAMPLES

Next, Production Examples for showing processes for the production of the starting compounds for the compounds of the present invention and Examples for showing representative examples of the compounds of the present invention will be given. However it is to be understood that the present invention is not restricted thereto. When the compound described in the production example was a tricyclic compound having a nitro group, the nitro group was reduced into an amino group via catalytic reduction with the use of a catylyst such as palladium-carbon or platinum oxide or reduction effected by adding hydrochloric acid or acetic acid to zinc, iron, etc., and then the resulting compound was reacted with an aromatic sulfonyl chloride to thereby give the compound described in the corresponding example.

Production Example 1

2-Benzyloxy-5-nitro-9(10H)-acridinone

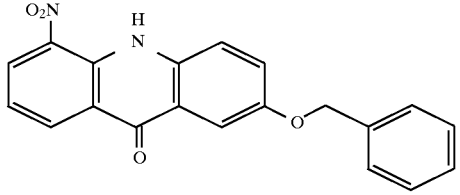

A mixture comprising 2.2 g (11 mmol.) of 4-benzyloxyaniline, 2.0 g (10 mmol) of 2-chloro-3-nitrobenzoic acid, 6 ml of N,N-dimethylaniline and 1.6 ml of N,N-diisopropylethylamine was heated at 100° C. for 12 hours under stirring. After cooling, 30 ml of chloroform and 30 ml of 1N sodium hydroxide were added thereto. The precipitate thus formed was separated by filtration, stirred together with 5% hydrochloric acid and washed with water to thereby give 3.3 g of 2-((4-benzyloxyphenyl)amino)-3-nitrobenzoic acid. This product was added to 40 ml of chloroform and 0.3 ml of N,N-dimethylaniline and 6 ml of phosphorus oxychloride were further added thereto. After heating under reflux for 30 minutes and then cooling, the crystals thus precipitated were separated by filtration. Thus 2.1 g of the title compound was obtained.

$^1$H-NMR(DMSO-$d_6$) δ(ppm): 5.22(2H, s), 7.33(1H, t, J=8.0 Hz), 7.36–7.42(3H, m), 7.49(2H, d, J=8.0 Hz), 7.54 (1H, dd, J=9.2, 2.8 Hz), 7.69(1H, d, J=2.8 Hz), 8.08(1H, d, J=9.2 Hz), 8.65–8.69(2H, m), 11.5(1H, br s)

Production Example 2

7-Fluoro-1-nitro-10H-phenothiazine

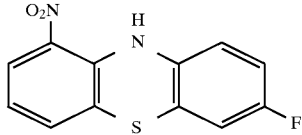

2.2 g (15 mmol) of 2-amino-5-fluorobenzenethiol was dissolved in 30 ml of dimethylformamide and 2.5 g (12 mmol) of 1-chloro-2,6-dinitrobenzene was added thereto. The resulting mixture was stirred at room temperature. After 12 hours, 2.6 ml of N,N-diisopropylethylamine was added thereto and the mixture was heated at 80° C. for 2 hours. After cooling, the reaction mixture was poured into a saturated aqueous solution of ammonium chloride and extracted with ethyl acetate. After concentrating, the residue was purified by silica gel column chromatography. Thus 1.2 g of the title compound was obtained.

$^1$H-NMR(CDCl$_3$) δ(ppm): 6.64(1H, dd, J=8.8, 4.8 Hz), 6.70(1H, dd, J=8.0, 2.8 Hz), 6.73–6.80(2H, m), 7.12–7.15 (1H, m), 7.90(1H, dd, J=9.2, 1.4 Hz), 9.66(1H, br s)

Production Example 3

4-Amino-5H-dibenz[b,f]azepine

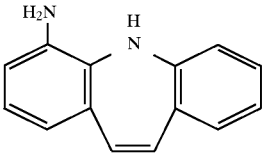

1 g (5.2 mmol) of 5H-dibenz(b,f)azepine was suspended in 40 ml of dry ether and 9.7 ml (15.5 mmol) of a 1.6M solution of n-butyllithium in hexane was dropped thereinto under stirring at room temperature. After 24 hours, the reaction mixture was cooled in a dry ice-acetone bath and 2 ml of a solution of 0.93 g (7.8 mmol) of isobutyl nitrate in dry ether was dropped thereinto. After stirring at room temperature for 30 minutes, 2 ml of acetic acid was added thereto. Then the reaction mixture was poured into 50 ml of water and extracted with ethyl acetate. The organic layer was washed with water, dried over magnesium sulfate and concentrated. Then the residue was purified by silica gel column chromatography to thereby give 4-nitro-5H-dibenz(b,f) azepine. This product was dissolved in 50 ml of tetrahydrofuran and 1 g of zinc dust was added. Under stirring, conc. hydrochloric acid was dropped thereinto. When the reaction mixture turned from reddish brown into pale yellow, the addition was ceased and the formed insoluble matters were filtered off. The filtrate was made basic by adding diluted aqueous ammonia and then extracted with ethyl acetate. The organic layer was washed with water, dried over magnesium sulfate and concentrated and the residue was purified by silica gel column chromatography. Thus 45 mg of the title compound was obtained.

Production Example 4

7-Hydroxy-1-nitro-10H-phenoxazine

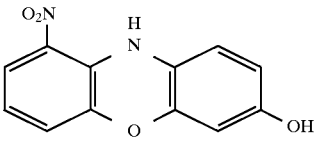

6 g (30 mmol) of 1-chloro-2,6-dinitrobenzene and 4.8 g (30 mmol) of 4-aminoresorcinol hydrochloride were added to 300 ml of a mixture of tetrahydrofuran with dimethylformamide (1:1). After adding 7.8 g (60 mmol) of N,N-diisopropylethylamine thereto, the obtained mixture was stirred at room temperature for 24 hours. Then the solvent was distilled off under reduced pressure and the residue was dissolved in ethyl acetate and washed with a saturated aqueous solution of sodium chloride. Then it was dried over magnesium sulfate and concentrated and the residue was purified by silica gel column chromatography. Thus 6.95 g of 4-((2,6-dinitrophenyl)amino)resorcinol was obtained. This product was dissolved in 125 ml of dimethylformamide and 25 ml of N,N-diisopropylethylamine was added thereto. After heating at 100° C. for 2 hours, the reaction mixture was concentrated and the residue was dissolved in ethyl acetate, washed with water, dried over magnesium sulfate and concentrated to dryness. Thus 5.4 g of the title compound was obtained.

Production Example 5

7-(tert-Butyldimethylsilyloxy)-1-nitro-10H-phenoxazine

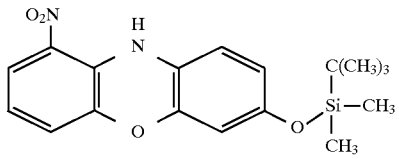

1.2 g (4.9 mmol) of the compound of Production Example 4, 1.1 g (7.4 mmol) of tert-butyldimethylsilyl chloride and 0.5 g (7.4 mmol) of imidazole were dissolved in 50 ml of dimethylformamide and stirred in a nitrogen atmosphere at room temperature for 8 hours. After concentrating, the residue was dissolved in 500 ml of diethyl ether, washed with water, dried over magnesium sulfate and concentrated. The residue was purified by silica gel column chromatography. Thus 1.15 g of the title compound was obtained.

Production Example 6

5,11-Dihydro-6-nitrodibenz(b,e)(1,4)oxazepine

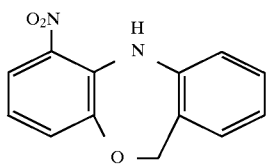

2.85 g (14 mmol) of 1-chloro-2,6-dinitrobenzene and 1.73 g (14 mmol) of 2-aminobenzyl alcohol were dissolved in 30 ml of triethylamine and heated under reflux for 24 hours. After concentrating, the residue was purified by silica gel column chromatography. Thus 2.2 g of 2-((2,6-dinitrophenyl)amino)benzyl alcohol was obtained. 0.29 g (1 mmol) of this powder was dissolved in 20 ml of dry dimethylformamide. After adding 40 mg (1 mmol) of sodium hydride (in oil, content: 60%), the reaction mixture was stirred at room temperature for 15 minutes and then at 150° C. for 2 hours. After cooling, 200 ml of ethyl acetate was added thereto and the mixture was washed with water, dried over magnesium sulfate and concentrated. The residue was purified by silica gel column chromatography. Thus 0.14 g of the title compound was obtained.

Production Example 7

9-Nitrodibenz(b,f)(1,4)oxazepin-11(10H)-one

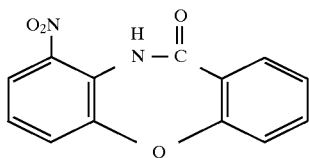

1.57 g (10 mmol) of 2-amino-3-nitrophenol was dissolved in 20 ml of pyridine and 3.36 g (21 mmol) of 2-fluorobenzoyl chloride was added thereto under stirring. After heating under reflux for 4 hours, the mixture was concentrated. Then dilute hydrochloric acid and ethyl acetate were added thereto. The organic layer was separated and washed with water. After concentrating, 20 ml of tetrahydrofuran and 20 ml of 1N sodium hydroxide were added and the mixture was heated under reflux for 4 hours. After cooling, it was neutralized with hydrochloric acid and concentrated. After adding ethyl acetate and water, the organic layer was separated, washed with water and dried over magnesium sulfate. After concentrating, the residue was purified by silica gel column chromatography. Thus 2.35 g of 2-fluoro-N-(2-hydroxy-6-nitrophenyl)benzamide was obtained. 553 mg (2 mmol) of this powder was dissolved in 20 ml of dimethylformamide and 332 mg (2.4 mmol) of potassium carbonate and 20 mg of a copper powder were added thereto. After heating under reflux for 3 hours and concentrating, ethyl acetate and dilute hydrochloric acid were added to the residue. The formed insoluble matters were filtered off and the organic layer was separated, washed with water, dried over magnesium sulfate and concentrated. Then the residue was purified by silica gel column chromatography. Thus 400 mg of the title compound was obtained.

M.p.: 162°–163° C.

Production Example 8

9,10-Dihydro-4-nitroacridine

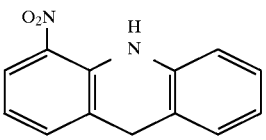

1.361 g (10 mmol) of aluminum chloride was dissolved in 10 ml of dry tetrahydrofuran. To the solution thus obtained was slowly added 75 ml of a solution of 1.201 g (5 mmol) of 4-nitro-9(10H)-acridinone in dry tetrahydrofuran. After stirring at room temperature for 30 minutes, 759 mg (20 mmol) of lithium aluminum hydride was added thereto in portions. After stirring at room temperature for 30 minutes and then at 55° C. for additional 30 minutes, the reaction mixture was cooled to room temperature and 5 ml of 1N hydrochloric acid was added thereto. After concentrating, ethyl acetate and water were added to the residue and the formed insoluble matters were filtered off. The organic layer was separated from the filtrate and dried over magnesium sulfate. After concentrating, the residue was purified by silica gel column chromatography. Thus 148 mg of the title compound was obtained.

$^1$H-NMR(CDCl$_3$) δ(ppm): 5.23(2H, br), 6.94(1H, dd, J=5.6, 2.8 Hz), 7.32–7.38(2H, m), 7.48–7.55(1H, m), 7.69–7.75(1H, m), 7.94–8.00(1H, m), 8.18–8.24(1H, m), 8.67(1H, s)

Production Example 9

5,11-Dihydro-6-nitrodibenzo[b,e][1,4]thiazepine

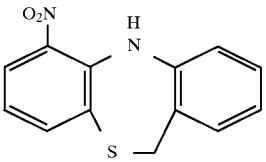

1.8 g (6.2 mmol) of 2-((2,6-dinitrophenyl)amino)benzyl alcohol was dissolved in a mixture of 50 ml of dichloromethane with 50 ml of ethyl ether. Under ice-cooling and stirring, 2.2 ml (15.5 mmol) of triethylamine and 0.58 ml (7.4 mmol) of methanesulfonuyl chloride were successively added thereto. After stirring for 30 minutes, the reaction mixture was poured into a saturated aqueous solution of ammonium chloride and extracted with ethyl acetate. After concentrating, the residue was dissolved in 150 ml of acetone. Then 2.7 g (31 mmol) of lithium bromide was added and the resulting mixture was heated under reflux for 1 hour. After distilling off the solvent under reduced pressure, the residue was purified by silica gel column chromatography to thereby give 0.5 g of 2((2,6-dinitrophenyl)amino)benzyl bromide. Thio product was dissolved in 10 ml of dimethylformamide. After adding 216 mg (2.8 mmol) of thiourea, the mixture was stirred at room temperature for 5 hours. Then 10 ml of dimethylformamide, 157 mg (2.8 mmol) of potassium hydroxide and 2 ml of water were successively added thereto and the reaction mixture was heated at 100° C. for 3 hours. After cooling, the reaction mixture was poured into a saturated aqueous solution of sodium chloride and extracted with ethyl acetate. After concentrating, the residue was purified by silica gel column chromatography. Thus 0.22 g of the title compound was obtained.

$^1$H-NMR(CDCl$_3$) δ(ppm): 4.02(2H, s), 6.73(1H, dd, J=8.8, 7.6 Hz), 6.94(1H, dt, J=7.6, 1.2 Hz), 7.06(1H, dd, J=7.6, 1.6 Hz), 7.09(1H, dd, J=7.6, 1.2 Hz), 7.22(1H, dt, J=7.6, 1.6 Hz), 7.55(1H, dd, J=7.6, 1.6 Hz), 8.17(1H, dd, J=8.8, 1.6 Hz), 11.13(1H, br s)

Production Example 10

N$^2$-(4-Methylphenyl)-1,2,3-triaminobenzene

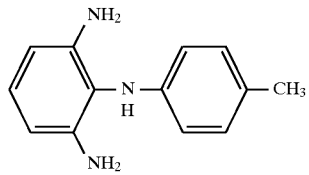

0.8 g (7.4 mmol) of p-toluidine and 1.5 g of 1-chloro-2,6-dinitrobenzene were dissolved in 15 ml of dimethyl sulfoxide and 1.5 g (14.8 mmol) of triethylamine was added thereto. After stirring at 80° to 90° C. for 12 hours, ethyl acetate was added and the reaction mixture was washed with water and dried over magnesium sulfate. After concentrating, the residue was purified by silica gel column chromatography. Thus 2.0 g of N-(4-methylphenyl)-2,6-dinitroaniline was obtained. This product was dissolved in a mixture of 20 ml of methanol with 40 ml of tetrahydrofuran and hydrogenated in the presence of palladium-carbon at room temperature under atmospheric pressure. After filtering off the catalyst, the solvent was distilled off under reduced pressure. Thus 1.6 g of the title compound was obtained.

$^1$H-NMR(CDCl$_3$) δ(ppm): 2.25(3H, s), 3.75(4H, br), 4.68 (1H, br s), 6.23(2H, d, J=8.0 Hz), 6.56(2H, dd, J=8.0, 2.0 Hz), 6.92(1H, t, J=8.0 Hz), 6.99(2H, d, J=8.0 Hz)

Production Example 11

N-(3-Amino-2-((4-methylphenyl)amino)phenyl)-4-methoxybenzenesulfonamide

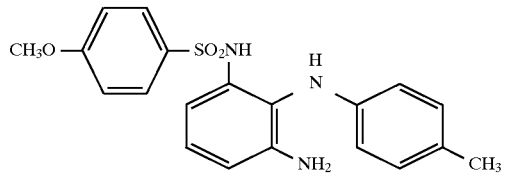

1.6 g (7.4 mmol) of the compound of Production Example 10 was dissolved in 40 ml of tetrahydrofuran. Then 5.6 ml of pyridine and 1.7 g (8.1 mmol) of 4-methoxybenzenesulfonyl chloride were successively added thereto. After stirring at room temperature for 12 hours, ethyl acetate was added. The reaction mixture was washed with water, dried over magnesium sulfate and concentrated. Then the residue was purified by silica gel column chromatography. Thus 1.8 g of the title compound was obtained.

$^1$H-NMR(CDCl$_3$) δ(ppm): 2.24(3H, s), 3.65(2H, br), 3.85 (3H, s), 4.62(1H, br s), 6.28(2H, d, J=8.4 Hz), 6.49(1H, dd, J=8.0, 1.6 Hz), 6.86(2H, d, J=8.8 Hz), 6.90(2H, d, J=8.4 Hz), 6.96(2H, dd, J=8.0, 1.6 Hz), 7.02(1H, t, J=8.0 Hz), 7.22(1H, br s), 7.67(2H, d, J=8.8 Hz)

Production Example 12

2-((2,6-Dinitrophenyl)amino)-5-fluorobenzoic acid

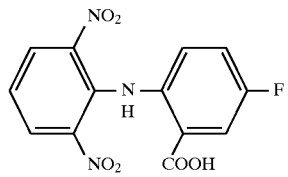

3.0 g (19.3 mmol) of 2-amino-5-fluorobenzoic acid and 5.88 g (29.0 mmol) of 1-chloro-2,6-dinitrobenzene were dissolved in a mixture of 30 ml of dimethylformamide with 30 ml of dimethyl sulfoxide. After adding 6.74 ml of triethylamine, the reaction mixture was stirred in a nitrogen atmosphere at room temperature for 14 days and concentrated followed by the addition of 1N hydrochloric acid thereto. Then it was extracted with ethyl acetate, washed with 1N hydrochloric acid and dried over magnesium sulfate. After concentrating, chloroform was added thereto. The crystals thus precipitated were collected. Thus 2.65 g of the title compound was obtained.

$^1$H-NMR(DMSO-d$_6$) δ(ppm): 6.88(1H, dd, J=9.2, 4.4 Hz), 7.29–7.4(1H, m), 7.37(1H, t, J=8.0 Hz), 7.6(1H, dd, J=9.2, 3.2 Hz), 8.35(2H, d, J=8.0 Hz), 10.70(1H, s), 13.87 (1H, br s)

Production Example 13

6-Amino-5,10-dihydro-2-fluoro-11H-dibenzo,(b,e)(1,4)-diazepin-11-one

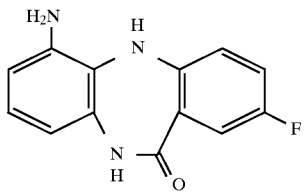

2.5 g (7.8 mmol) of the compound of Production Example 12 was dissolved in a mixture of 30 ml of tetrahydrofuran with 5 ml of methanol and then hydrogenated in the presence of palladium hydroxidecarbon under a hydrogen atmosphere of 3 kg/cm$^2$. After filtering off the catalyst and distilling off the solvent under reduced pressure, the residue was dissolved in 25 ml of dimethylformamide. After adding 4.5 ml (19.5 mmol) of diphenylphosphoryl azide and 6.5 ml (46.7 mmol) of triethylamine, the mixture was stirred at room temperature for 4 days. Then it was concentrated and a saturated aqueous solution of ammonium chloride was added thereto. Then it was extracted with ethyl acetate and washed successively with a saturated aqueous solution of ammonium chloride and a saturated aqueous solution of sodium chloride. After drying over magnesium sulfate and concentrating, the residue was purified by silica gel column chromatography. Thus 1.53 g of the title compound was obtained.

$^1$H-NMR(DMSO-d$_6$) δ(ppm): 5.22(2H, br s), 6.27(1H, dd, J=8.0, 1.2 Hz), 6.43(1H, dd, J=8.8, 1.2 Hz), 6.67(1H, t, J=8.0 Hz), 6.82(1H, br s), 7.16–7.27(2H, m), 7.35(1H, dd, J=9.6, 3.2 Hz), 9.88(1H, br s)

Example 1

4-Methoxy-N-(10H-phenothiazin-1-yl)benzenesulfonamide

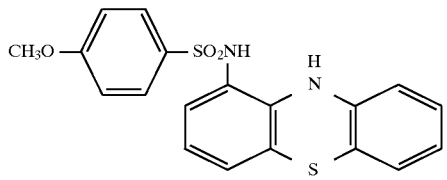

107 mg (0.5 mmol) of 1-amino-10H-phenothiazine was dissolved in 4 ml of pyridine. Then 2 ml of a solution of 115 mg (0.55 mmol) of 4-methoxybenzenesulfonyl chloride in tetrahydrofuran was added thereto under stirring at room temperature. After stirring at room temperature overnight, the reaction mixture was concentrated. Then ethyl acetate and water were added to the residue and the organic layer was separated, washed with water and dried over magnesium sulfate. After concentrating, the residue was purified by silica gel column chromatography and recrystallized from ethanol. Thus 115 mg of the title compound was obtained.

M.p.: 158°–160° C.

$^1$H-NMR(DMSO-d$_6$) δ(ppm): 3.74(3H, s), 6.60(1H, dd, J=8.0, 1.6 Hz), 6.65(1H, t, J=8.0 Hz), 6.70(1H, dd, J=8.0, 1.2 Hz), 6.77–6.84(2H, m), 6.93(1H, dd, J=7.6, 1.2 Hz), 6.96–7.02(3H, m), 7.57(2H, d, J=8.8 Hz), 7.62(1H, br s), 9.39(1H, br s)

Example 2

N-(9H-Carbazol-1-yl)-4-methoxybenzenesulfonamide

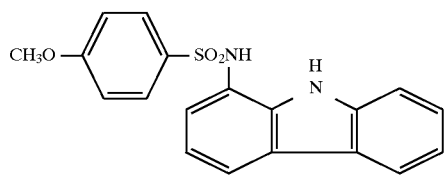

The title compound was obtained by a method similar to the one described in Example 1.

M.p.: 201°–202° C.

Example 3

N-(9,10-Dihydroacridin-4-yl)-4-methoxybezenesulfonamide

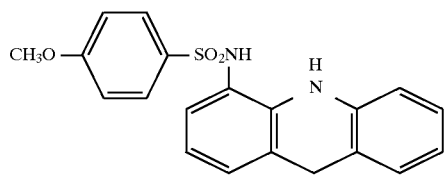

The title compound was obtained by a method similar to the one described in Example 1.

$^1$H-NMR(DMSO-d$_6$) δ(ppm): 3.71(3H, s), 3.87(2H, s), 6.58–6.65(2H, m), 6.74–6.80(2H, m), 6.88–6.92(1H, m), 6.94–7.04(4H, m), 7.57(2H, d, J=8.8 Hz) 7.62(1H, br s), 9.29(1H, br s)

Example 4

N-(9(10H)-Acridinon-4-yl)-4-methoxybenzenesulfonamide

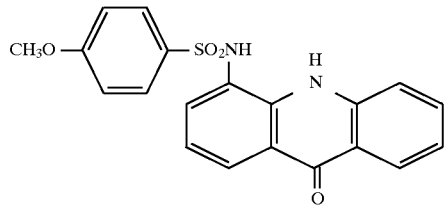

The title compound was obtained by a method similar to the one described in Example 1.

$^1$H-NMR(DMSO-d$_6$) δ(ppm): 3.75(3H, s), 7.02(2H, d, J=8.8 Hz), 7.05–7.15(2H, m), 7.24–7.32(1H, m), 7.62(2H, d, J=8.8 Hz), 7.70–7.77(1H, m), 7.84(1H, d, J=8.8 Hz), 8.07–8.13(1H, m), 8.19(1H, dd, J=8.0, 1.2 Hz), 9.74(1H, br s), 10.79(1H, br s)

Example 5

4-Methoxy-N-(10H-phenoxazin-1-yl)benzenesulfonamide

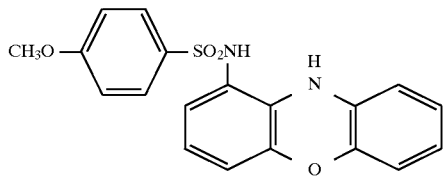

The title compound was obtained by a method similar to the one described in Example 1.

M.p.: 220°–223° C. (decomp.).

Example 6

N-(10,11-Dihydro-5H-dibenz(b,f)azepin-4-yl)-4-methoxybenzenesulfonamide

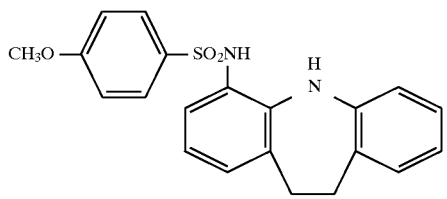

The title compound was obtained by a method similar to the one described in Example 1.

M.p.: 182.5°–184.5° C.

$^1$H-NMR(DMSO-d$_6$) δ(ppm): 2.78–2.92(4H, m), 3.64 (3H, s), 6.56–6.70(4H, m), 6.82(2H, d, J=8.8 Hz), 6.88–6.95 (2H, m), 6.97–7.03(1H, m), 7.26(1H, br s), 7.44(2H, d, J=8.8 Hz), 9.47(1H, br s)

Example 7

N-(7-Methoxy-9(10H)-acridinon-4-yl)-4-methoxybenzenesulfonamide

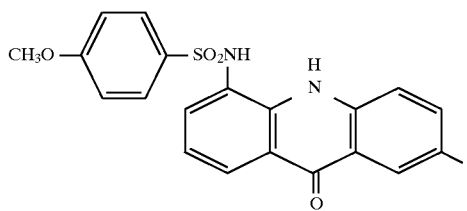

The title compound was obtained by a method similar to the one described in Example 1.

M.p.: 253°–256° C. (decomp.).

$^1$H-NMR(DMSO-d$_6$) δ(ppm): 3.76(3H, s), 3.86(3H, s), 7.00–7.08(4H, m), 7.42(1H, dd, J=8.8, 3.2 Hz), 7.58(1H, d, J=3.2 Hz), 7.62(2H, d, J=8.8 Hz), 7.86 (1H, d, J=8.8 Hz), 8.10(1H, dd, J=7.62, 2.0 Hz), 9.72(1H, br s), 10.84(1H, br s)

Example 8

4-Methoxy-N-(7-methoxy-10H-phenothiazin-1-yl)benzenesulfonamide

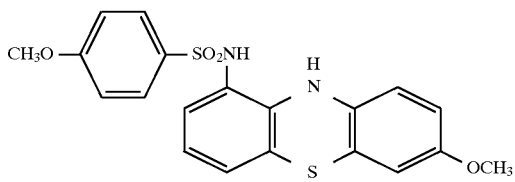

The title compound was obtained by a method similar to the one described in Example 1.

M.p.: 157°–160° C.

Example 9

N-(5H-Dibenz[b,f]azepin-4-yl)-4-methoxybenzenesulfonamide

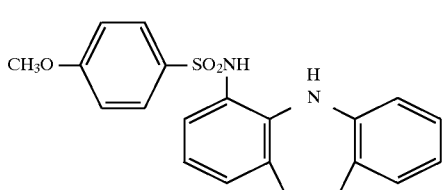

The title compound was obtained by a method similar to the one described in Example 1.

$^1$H-NMR(DMSO-d$_6$) δ(ppm): 3.78(3H, s), 6.13–6.24(2H, m), 6.33–6.41(3H, m), 6.55(1H, t J=7.6 Hz), 6.65–6.82(3H, m), 6.93–6.99(1H, m), 7.03(2H, d, J=8.8 Hz), 7.59(2H, d, J=8.8 Hz), 9.38(1H, br s)

Example 10

4-Methoxy-N-(6(5H)-phenanthridinon-4-yl)benzenesulfonamide

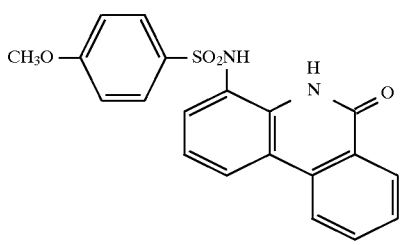

The title compound was obtained by a method similar to the one described in Example 1.

$^1$H-NMR(DMSO-d$_6$) δ(ppm): 3.73(3H, s), 6.99(2H, d, J=8.8 Hz), 7.08(1H, d, J=7.6 Hz), 7.16(1H, t, J=7.6 Hz), 7.58(2H, d, J=8.8 Hz), 7.65(1H, t, J=7.6 Hz), 7.85(1H, t, J=7.6 Hz), 8.20–8.35(2H, m) 8.49(1H, d, J=8.4 Hz), 9.80 (1H, br s), 10.20(1H, br s)

Example 11

N-(7-Flouro-10H-phenothiazin-1-yl-4-methoxybenzenesulfonamide

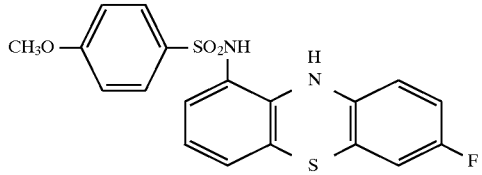

The title compound was obtained by a method similar to the one described in Example 1.

M.p.: 166°–168° C.

Example 12

N-(Dibenz(b,f)(1,4)oxazepin-11(10H)-on-9-yl)-4-methoxybenzenesulfonamide

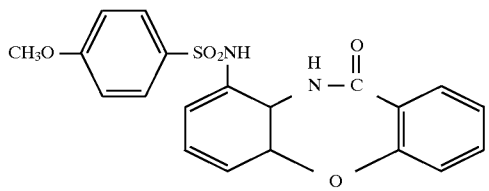

The title compound was obtained by a method similar to the one described in Example 1.

M.p.: 239.5°–241° C.

Example 13

N-(7-Hydroxy-10H-phenothiazin-1-yl)-4-methoxybenzenesulfonamide

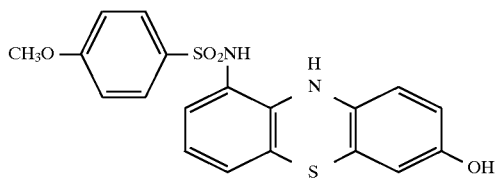

The title compound was obtained by a method similar to the one described in Example 1.

$^1$H-NMR(DMSO-d$_6$) δ(ppm) 3.73(3H, s), 6.36(1H, d, J=2.8 Hz), 6.41(1H, dd, J=8.4, 2.8 Hz), 6.52(1H, d, J=8.4 Hz), 6.58(1H, dd, J=6.4, 2.8 Hz), 6.60(1H, t, J=6.4 Hz), 6.80(1H, dd, J=6.4, 2.8 Hz), 6.98(2H, d, J=8.8 Hz), 7.30(1H, br s), 7.55(2H, d, J=8.8 Hz), 9.08(1H, br s), 9.38(1H, br s)

Example 14

N-(4-Acridinyl)-4-methoxybenzenesulfonamide

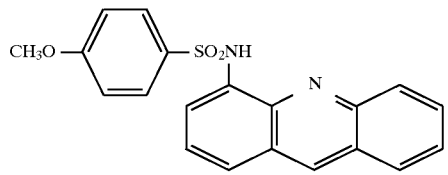

The title compound was obtained by a method similar to the one described in Example 1.

M.p.: 143°–145° C.

Example 15

4-Methoxy-N-(10H-pyrido-(3,2-b)(1,4)benzoazin-9-yl-benzenesulfonamide

The title compound was obtained by a method similar to the one described in Example 1.

$^1$H-NMR(DMSO-d$_6$) δ(ppm): 3.77(3H, s), 6.51–6.60(3H, m), 6.63(1H, dd, J=7.6, 5.2 Hz), 6.92(1H, dd, J=7.6, 1.2 Hz), 7.05(2H, d, J=9.2 Hz), 7.57(1H, dd, J=5.2, 1.2 Hz), 7.63(2H, d, J=9.2 Hz), 7.82(1H, br s), 9.37(1H, br s)

Example 16

4-Methoxy-N-(5H-pyrido(2,3-b)(1,4)benzoxazin-6-yl)-benzenesulfonamide

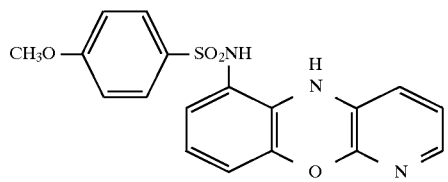

The title compound was obtained by a method similar to the one described in Example 1.

$^1$H-NMR(DMSO-d$_6$) δ(ppm): 3.80(3H, s), 6.16(1H, d, J=8.0 Hz), 6.43(1H, t, J=8.0 Hz), 6.56(1H, d, J=8.0 Hz), 6.78(1H, dd, J=7.6, 5.2 Hz), 7.00(1H, dd, J=7.6, 1.6 Hz), 7.07(2H, d, J=8.8 Hz), 7.39(1H, dd, J=5.2, 1.6 Hz), 7.65(2H, d, J=8.8 Hz), 7.82(1H, br s), 9.15(1H, br s)

Example 17

N-(5,11-Dihydrodibenz(b,e)(1,4)oxazepin-6-yl)-4-methoxybenzenesulfonamide

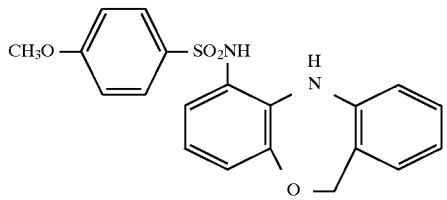

The title compound was obtained by a method similar to the one described in Example 1.

M.p.: 153.5°–155° C.

$^1$H-NMR(DMSO-d$_6$) δ(ppm): 3.65(3H, s), 4.83(2H, s), 6.53–6.59(2H, m), 6.73(1H, t, J=7.6 Hz), 6.77(1H, d, J=7.6 Hz), 6.81(1H, dd, J=7.0, 3.7 Hz), 6.91(2H, d, J=8.8 Hz), 7.04(1H, d, J=7.6 Hz), 7.15(1H, t, J=7.6 Hz), 7.34(1H, br s), 7.53(2H, d, J=8.8 Hz), 9.48(1H, br s)

Example 18

4-Methoxy-N-(10H-phenothiazin-1-yl)benzenesulfonamide S-oxide

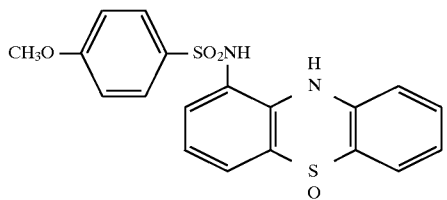

200 mg (0.516 mmol) of the compound of Example 1 was dissolved in 20 ml of dichloromethane and 111 mg (0.645 mmol) of m-chloroperbenzoic acid was added thereto under ice-cooling and stirring. After stirring for 30 minutes, the crystals thus precipitated were collected by filtration and recrystallized from methanol-ethyl ether-dichloromethane. Thus 150 mg of the title compound was obtained.

M.p.: 221°–223° C. (decomp.).

Example 19

4-Methoxy-N-(10H-phenothiazin-1-yl)benzenesulfonamide S,S-dioxide

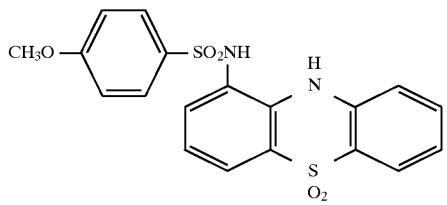

210 mg (0.56 mmol) of the compound of Example 1 was dissolved in 20 ml of dichloromethane and 242 mg (1.40 mmol) of m-chloroperbenzoic acid was added thereto under ice-cooling and stirring. After stirring at room temperature for 12 hours, the crystals thus precipitated were collected by filtration and recrystallized from ethanol. Thus 170 mg of the title compound was obtained.

M.p.: 247°–249° C.

Example 20

N-(7-Hyrdroxy-9(10H)-acridinon-4-yl)-4-methoxybenzenesulfonamide

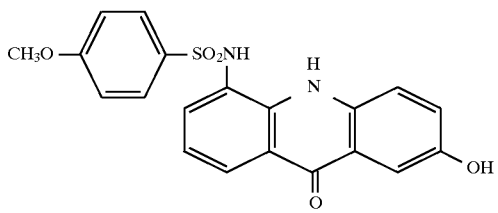

0.47 g (1.5 mmol) of the compound of the Production Example 1 was dissolved in a mixture of 50 ml of methanol with 150 ml of ethyl acetate. After adding 50 mg of platinum oxide, hydrogenation was effected at room temperature under atmospheric pressure. After filtering off the formed insoluble matters, the mixture was concentrated to dryness to thereby give 5-amino-2-benzyloxy-9(10H)-acridinone. This product was dissolved in 20 ml of pyridine and 5 ml of a solution of 0.32 g (1.5 mmol) of 4-methoxybenzenesulfonyl chloride in tetrahydrofuran was added thereto under stirring at room temperature. After stirring for 1 hour, the reaction mixture was poured into a saturated aqueous solution of sodium chloride and extracted with ethyl acetate. After concentrating, the residue was purified by silica gel column chromatography. The N-(7-benzyloxy-9-(10H)-acridinon-4-yl)-4-methoxybenzenesulfonamide thus obtained was dissolved in a mixture of 100 ml of methanol with 100 ml of ethyl acetate. After adding palladium-carbon, hydrogenation was effected at room temperature under atmospheric pressure. After filtering off the palladium-carbon and concentrating to dryness, 0.21 g of the title compound was obtained.

$^1$H-NMR(DMS-d$_6$) δ(ppm): 3.74(3H, s), 6.96–7.03(4H, m), 7.24(1H, dd, J=8.8, 2.8 Hz), 7.48(1H, d, J=2.8 Hz), 7.61(2H, d, J=8.8 Hz), 7.74(1H, d, J=8.8 Hz), 7.98(1H, d, J=7.6 Hz), 9.61(1H, br s), 10.63(1H, br s)

Example 21

N-(6-Hydroxy-9-(10H)-acridinon-4yl)-4-methoxybenzenesulfonamide

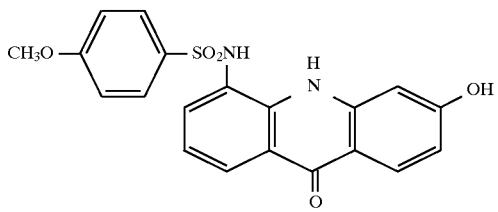

The title compound was obtained by a method similar to the one described in Example 20.

$^1$H-NMR(DMSO-d$_6$) δ(ppm): 3.73(3H, s), 6.72(1H, dd, J=8.8, 2.0 Hz), 6.96–7.07(5H, m), 7.59(2H, d, J=8.8 Hz), 8.00(2H, d, J=8.8 Hz), 9.71(1H, br s), 10.47(1H, br s), 10.49(1H, br s)

Example 22

N-(7-Hydroxy-10H-phenoxazin-1-yl)-4-methoxybenzenesulfonamide

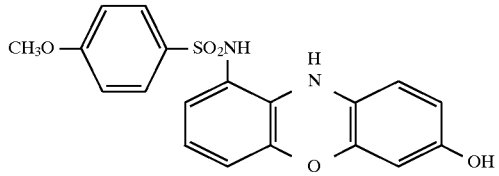

1.15 g (3.2 mmol) of the compound of Production Example 5 was dissolved in 30 ml of tetrahydrofuran. After adding palladium-carbon thereto, hydrogenation was effected at room temperature under atmospheric pressure. Then the palladium-carbon was filtered off and the solution was concentrated to approximately halve the volume. After adding 5 ml of pyridine and 0.72 g (3.5 mmol) of 4-methoxybenzenesulfonyl chloride thereto, the obtained mixture was stirred at room temperature overnight. Then ethyl acetate and water were added and the organic layer was separated, washed with water, dried over magnesium sulfate and concentrated. Then the residue was purified by silica gel column chromatography to thereby give 1.5 g of N-[7-(tert-butyldimethylsilyloxy)-10H-phenoxazin-1-yl]-4-methoxybenzenesulfonamide. 0.5 g (1 mmol) of this compound was dissolved in 10 ml of tetrahydrofuran and 1.2 ml of a 1M solution of tetra-n-butylammonium fluoride in hexane was added thereto in a nitrogen atmosphere. After stirring at room temperature for 10 minutes, 1.5 ml of 1N hydrochloric acid and ethyl acetate were added to the reaction mixture. The organic layer was washed with water, dried over magnesium sulfate and concentrated to dryness. Thus 0.26 g of the title compound was obtained.

$^1$H-NMR(DMSO-d$_6$) δ(ppm): 3.79(3H, s), 6.09(1H, d, J=2.4 Hz), 6.17(1H, dd, J=8.4, 2.4 Hz), 6.27(1H, dd, J=8.0, 1.6 Hz), 6.37(1H, t, J=8.0 Hz), 6.45(1H, d, J=8.4 Hz), 6.45(1H, dd, J=8.0, 1.6 Hz), 7.06(2H, d, J=8.8 Hz), 7.06(1H, br s), 7.65(2H, d, J=8.8 Hz), 8.97(1H, br s), 9.10(1H, br s)

Example 23

N-(9H-Carbazol-1-yl)-3-chlorobenzenesulfonamide

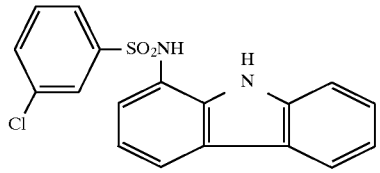

The title compound was obtained by a method similar to the one described in Example 1.

M.p.: 162.5°–163.5° C.

Example 24

4-Methoxy-N-(3H-phenoxazin-3-on-9-yl)benzenesulfonamide

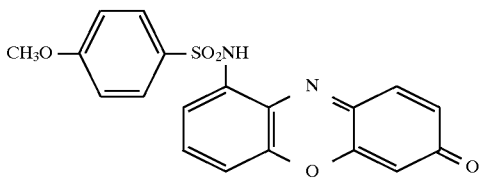

0.12 g (0.51 mmol) of the compound of Production Example 4 was dissolved in 20 ml of tetrahydrofuran. After adding palladium-carbon thereto, hydrogenation was effected at room temperature under atmospheric pressure. Then the palladium-carbon was filtered off and the solution was concentrated to approximately halve the volume. After adding 3 ml of pyridine and 0.12 g (0.56 mmol) of 4-methoxybenzenesulfonyl chloride thereto, the obtained mixture was stirred at room temperature overnight. After concentrating, the residue was purified by silica gel column chromatography. Thus 35 mg of the title compound was obtained.

$^1$H-NMR(CDCl$_3$) δ(ppm): 3.82(3H, s), 6.31(1H, d, J=2.0 Hz), 6.87(1H, dd, J=10.0, 2.0 Hz), 6.92(2H, d, J=8.8 Hz), 6.93(1H, dd, J=8.4, 1.2 Hz), 7.40(1H, d, J=10.0 Hz), 7.42(1H, t, J=8.4 Hz), 7.48(1H, dd, J=8.4, 1.2 Hz), 7.86(2H, d, J=8.8 Hz), 8.43(1H, br s)

Example 25

4-Methoxy-N-(3H-phenothiazin-3-on-9-yl)benzenesulfonamide

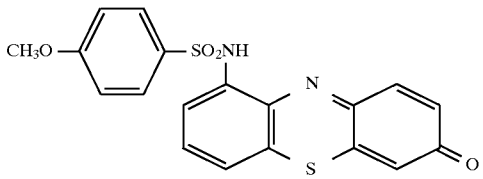

The title compound was obtained as a by-product of the synthesis of the compound of Example 13 from 4-methoxybenzenesulfonyl chloride and 1-amino-7-hydroxy-10H-phenothiazine.

$^1$H-NMR(DMSO-d$_6$) δ(ppm): 3.72(3H, s), 6.85(1H, d, J=2.0 Hz), 6.89(1H, dd, J=10.0, 2.0 Hz), 7.01(2H, d, J=8.8 Hz), 7.34–7.37(1H, m), 7.43–7.50(2H, m), 7.78(1H, d, J=10.0 Hz), 7.80(2H, d, J=8.8 Hz), 10.23(1H, br s)

Example 26

N-(5,11-Dihydrobenzo(b,e)(1,4)thiazepin-6-yl)-4-methoxybenzenesulfonamide

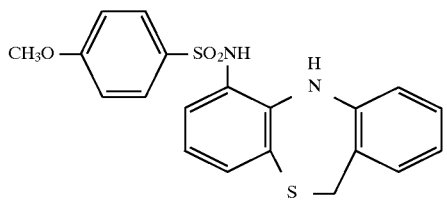

The title compound was obtained by a method similar to the one described in Example 1.
M.p.: 200°–202° C.

Example 27

N-(5,10-Dihydro-2-flouro-11H-dibenzo(b,e)(1,4)-diazepin-11-on-6-yl)-4-methoxybenzenesulfonamide

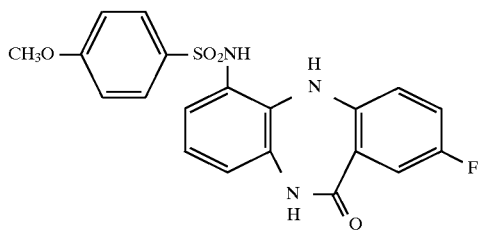

The title compound was obtained by reacting 4-methoxybenzenesulfonyl chloride with the compound of Production Example 13 in the same manner as that of Example 1.
M.p.: 241.5°–243° C.
$^1$H-NMR(DMSO-d$_6$) δ(ppm): 3.74(3H, s), 6.52(1H, dd, J=8.0, 1.2 Hz), 6.76(1H, dd, J=8.8, 4.8 Hz), 6.79(1H, t, J=8.0 Hz), 6.86(1H, dd, J=8.0, 1.2 Hz), 6.94(2H, d, J=8.8 Hz), 7.14(1H, td, J=8.8, 3.2 Hz), 7.14(1H, s), 7.32(1H, dd, J=9.6, 3.2 Hz), 7.47(2H, d, J=8.8 Hz), 9.54(1H, br s), 10.06(1H, s)

Example 28

N-(7,8-Difluoro-10H-phenothiazin-1-yl)-4-methoxybenzenesulfonamide

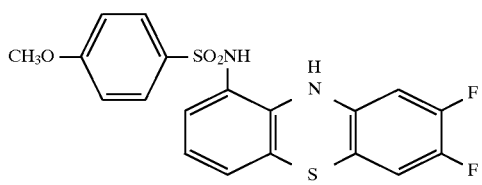

The title compound was obtained by a method similar to the one described in Example 1.
M.p.: 158°–160° C. (decomp.).
$^1$H-NMR(DMSO-d$_6$) δ(ppm): 3.76(3H, s), 6.54(1H, dd, J=8.0, 1.2 Hz), 6.70(1H, t, J=8.0 Hz), 6.85(1H, dd, J=12.4, 7.2 Hz), 6.89(1H, dd, J=8.0, 1.2 Hz), 7.01(2H, d, J=9.2 Hz), 7.17(1H, dd, J=10.4, 8.0 Hz), 7.55(2H, d, J=9.2 Hz), 7.88(1H, br s), 9.27(1H, br s)

Example 29

4-Methoxy-N-(10-methyl-10H-phenoxazin-1-yl)benzenesulfonamide

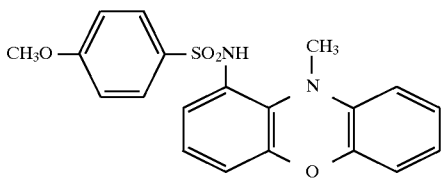

The title compound was obtained by a method similar to the one described in Example 1.
M.p.: 151°–153° C.
$^1$H-NMR(DMSO-d$_6$) δ(ppm): 3.27(3H, s), 3.80(3H, s), 6.22(1H, dd, J=8.0, 1.6 Hz), 6.58 (1H, t, J=8.0 Hz) 6.66(1H, dd, J=8.0, 1.6 Hz), 6.69(1H, dd, J=8.0, 1.6 Hz), 6.75(1H, dd, J=8.0, 1.6 Hz), 6.79(1H, td, Jt=7.8, Jd=1.6 Hz), 6.93(1H, td, Jt=8.0, Jd=1.6 Hz), 7.04(2H, d, J=8.8 Hz), 7.59(2H, d, J=8.8 Hz), 9.37(1H, br s)

Example 30

N-(5,11-Dihydro-2-hydroxydibenz(b,e)(1,4)oxazepin-6-yl)-4-methoxybenzenesulfonamide

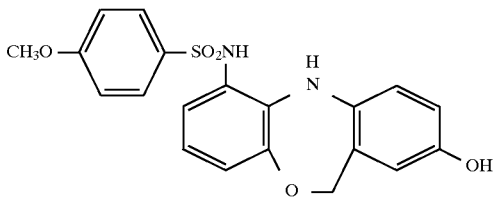

Starting with 2-(tert-butyldimethylsilyloxy)-5,11-dihydro-6-nitrodibenz(b,e)(1,4)oxazepine, which had been synthesized in the same manner as the one of Production Example 6, the title compound was obtained by a method similar to the one of Example 22.
M.p.: 200°–202° C.
$^1$H-NMR (DMSO-d$_6$) δ(ppm): 3.71(3H, s), 4.78(2H, s), 6.45(2H, d, J=4.8 Hz), 6.50(1H, s), 6.60(2H, s), 6.73(1H, t, J=4.8 Hz), 6.95(2H, d, J=8.8 Hz), 6.99(1H, br s), 7.55(2H, d, J=8.8 Hz), 8.96(1H, br s), 9.42(1H, br s)

Example 31

N-(10,11-Dihydro-2-methyl-5H-dibenzo(b,e)(1,4)-diazapin-6-yl)-4-methoxybenzenesulfonamide

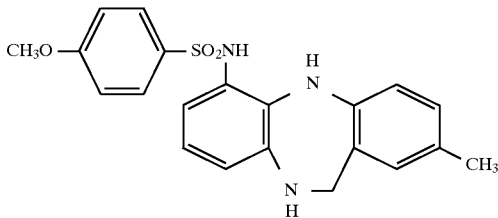

0.6 g (1.56 mmol) of the compound of Production Example 11 was dissolved in 30 ml of methanol and 70 mg of paraformaldehyde and 2.35 ml of 1N hydrochloric acid were added thereto. After heating under reflux for 30 minutes and adding ethyl acetate, the reaction mixture was washed with water and dried over magnesium sulfate. After concentrating, the residue was crystallized from ethyl acetate-n-hexane. Thus 0.5 g of the title compound was obtained.

M.p.: 187°–192° C. (gradually melting).

¹H-MMR(DMSO-d₆) δ(ppm): 2.17(3H, s), 3.71(3H, s), 3.95(2H, br), 5.70(1H, br), 6.14(1H, d, J=8.0 Hz), 6.37(1H, t, J=8.0 Hz), 6.56(1H, d, J=8.0 Hz), 6.58(1H, d, J=8.0 Hz), 6.76(1H, d, J=2.0 Hz), 6.86(1H, dd, J=8.0, 2.0 Hz), 6.95(2H, d, J=8.8 Hz), 6.97(1H, br s), 7.56(2H, d, J=8.8 Hz), 9.34(1H, br s)

Example 32

N-(10,11-Dihydro-2-fluoro-5H-dibenzo(b,e)(1,4)-diazepin-6-yl)-4-methoxybenzenesulfonamide

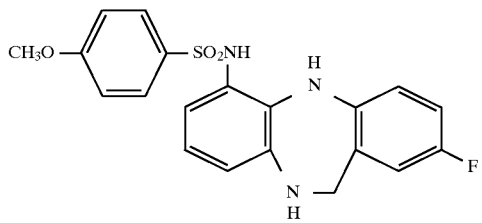

To 40 ml of a suspension of 460 mg (12.1 mmol) of lithium aluminum hydride in tetrahydrofuran was added 500 mg (1.2 mmol) of the compound of Example 27. After stirring at room temperature for 23 hours, ethyl acetate was added thereto in portions under ice-cooling. Then an aqueous solution of ammonium chloride was added thereto. After filtering off the formed insoluble matters, the filtrate was concentrated and an aqueous solution of ammonium chloride and ethyl acetate were added thereto. The organic layer was separated, washed with water, dried over magnesium sulfate and concentrated. Then the residue was purified by silica gel column chromatography and recrystallized from ethanol. Thus 315 mg of the title compound was obtained.

The title compound could be obtained also by the same synthesis route as the one of Example 31

M.p.: 180°–181° C.

¹H-MMR(DMSO-d₆) δ(ppm): 3.71(3H, s), 3.97(2H, br d, J=3.2 Hz), 5.76(1H, br t, J=3.2 Hz) 6.20(1H, dd, J=8.0, 1.6 Hz), 6.41(1H, t, J=8.0 Hz), 6.59(1H, dd, J=8.0, 1.6 Hz), 6.67(1H, dd, J=8.8, 5.2 Hz), 6.84–6.91(2H, m), 6.93(2H, d, J=8.8 Hz) 7.03(1H, br s), 7.54(2H, d, J=8.8 Hz), 9.34(3H, br s)

57 mg of the title compound was dissolved in a mixture of 3 ml of methanol and 6 ml of ethanol, then 1.4 ml of 1N hydrochloric acid was added thereto. After concentrating, ethanol was added and the crystals thus precipitated were separated by filtration and recrystallized from ethanol. Thus 23 mg of the hydrochloride of the title compound was obtained.

M.p.: 141.5°–143° C. (decomp.).

¹H-MMR(DMSO-d₆) δ(ppm): 3.62(3H, s), 4.27(2H, s), 6.76–6.85(1H, m), 6.82(2H, d, J=8.8 Hz), 6.85–6.94(2H, m), 6.97–7.08 (2H, m), 7.29(1H, br s), 7.43(2H, d, J=8.8 Hz), 7.93(1H, br s), 9.92(1H, br s)

Example 33

N-(7-Hydroxymethyl-10H-phenoaxazin-1-yl)-4-methoxybenzenesulfonamide

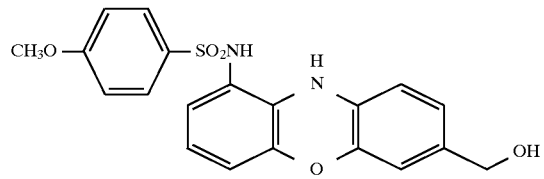

Starting with 7-((tert-butyldimethylsilyloxy)methyl)-1-nitro-10H-phenoxazine, the title compound was obtained by a method similar to that of Example 22.

M.p.: 230°–232.5° C.

¹H-MMR(DMSO-d₆) δ(ppm): 3.78(3H, s), 4.26(2H, d, J=5.6 Hz), 5.00(1H, t, J=5.6 Hz), 6.27(1H, dd, J=8.0, 2.4 Hz), 6.39(1H, t, J=8.0 Hz) 6.45(1H, br d, J=8.0 Hz), 6.54 (1H, d, J=1.2 Hz), 6.57 (1H, t, J=8.0 Hz), 6.67(1H, dd, J=8.0, 1.2 Hz) 7.05(2H, d, J=8.8 Hz), 7.34(1H, br s), 7.65(2H, d, J=8.8 Hz), 9.12(1H, br)

Example 34

4-Amino-N-(10H-phenothiazin-1-yl)benzenesulfonamide

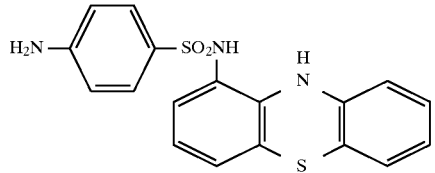

4-Nitrobenzenesulfonyl chloride was reacted with 1-amino-10H-phenothiazine in the same manner as the one of Example 11. The product thus obtained was hydrogenated in the presence of palladium-carbon at room temperature under atmospheric pressure. Thus the title compound was obtained.

¹H-MMR(DMSO-d₆) δ(ppm): 5.96(2H, br s), 6.49(2H, d, J=8.8 Hz), 6.53(1H, dd, J=8.0, 1.6 Hz), 6.62(1H, t, J=8.0 Hz), 6.77–6.82(3H, m), 6.93(1H, dd, J=7.6, 1.2 Hz), 7.01 (1H, dt, J=7.6, 1.2 Hz), 7.29(2H, d, J=8.8 Hz), 7.58(1H, br s), 9.14(1H, br s)

Example 35

4-Methoxy-N-(5H-pyrimido(4,5-b)(1,4)benzothiazin-6-yl)benzenesulfonamide

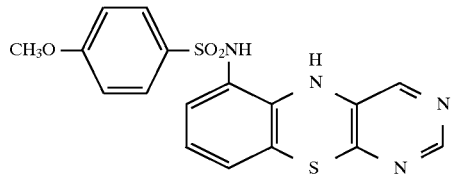

The title compound was obtained by a method similar to the one described in Example 1.

¹H-MMR(DMSO-d₆) δ(ppm): 3.75 (3H, s), 6.43(1H, br d, J=7.6 Hz), 6.63(1H, br t, J=7.6 Hz), 6.81 (1H, br d, J=7.6

Hz), 7.02(2H, d, J=9.2 Hz), 7.56(2H, d, J=9.2 Hz), 7.92(1H, br s), 7.94(1H, br s), 8.30(1H, br s), 9.28(1H, br s)

Example 36

4-Methoxy-N-(5H-pyrido(3,4-b)(1,4)benzothiazin-4-yl)benzenesulfonamide

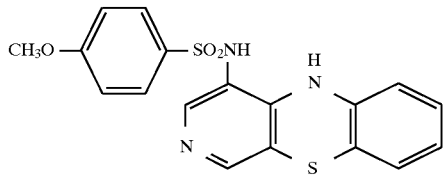

The title compound was obtained by a method similar to the one described in Example 1.

$^1$H-MMR(DMSO-d$_6$) δ(ppm): 3.73(3H, s), 6.80 (1H, dd, J=7.6, 1.2 Hz), 6.84 (1H, td, J=7.6, 1.2 Hz), 6.93 (1H, dd, J=7.6, 1.2 Hz), 7.00(1H, td, J=7.6, 1.2 Hz), 7.00(2H, d, J=9.2 Hz), 7.46(1H, s), 7.59 (2H, d, J=9.2 Hz), 7.72 (1H, s), 8.20(1H, s)

Example 37

N-(10-Acetyl-10,11-dihydro-5H-dibenzo(b,e)(1,4)-diazepin-6-yl)-4-methoxybenzenesulfonamide

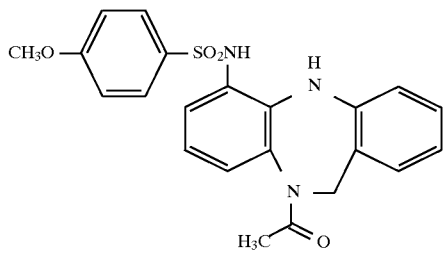

N-(10,11-Dihydro-5H-dibenzo(b,e)(1,4)diazepin-6-yl)-4-methoxybenzensulfonamide, which had been synthesized in the same manner as the one of Example 31, was reacted with acetic anhydride at room temperature. Then the obtained product was purified by silica gel column chromatography and thus the title compound was obtained.

$^1$H-MMR(DMSO-d$_6$) δ(ppm): 1.74(3H, s), 3.54(3H, s), 3.68(1H, d, J=14.8 Hz), 5.14(1H, d, J=14.8 Hz), 6.65–6.68 (2H, m), 6.78(2H, d, J=9.2 Hz), 6.81(1H, t, J=8.0 Hz), 6.96–7.06(3H, m), 7.16(1H, dd, J=8.0, 1.2 Hz), 7.37(1H, s), 7.40(2H, d, J=9.2 Hz), 9.60(1H, br s)

Example 38

N-(5,11-Dihydro-2-hydroxydibenz(b,e)(1,4)oxazepin-6-yl)-4-methylbenzenesulfonamide

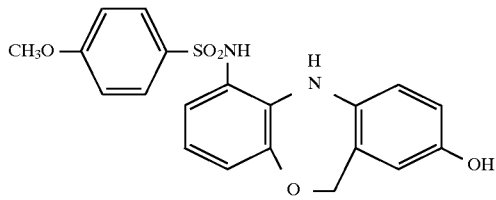

The title compound was obtained by a method similar to the one described in Example 30.

M.p.: 180.5°–182° C.

$^1$H-MMR(DMSO-d$_6$) δ(ppm): 2.24(3H, s), 4.78(2H, s), 6.42–6.49(2H, m), 6.50(1H, d, J=1.6 Hz), 6.56(1H, d, J=8.8 Hz), 6.60(1H, dd, J=8.8, 1.6 Hz), 6.74(1H, dd, J=5.2, 4.4 Hz), 6.95(1H, br s), 7.25(2H, d, J=8.0 Hz), 7.51(2H, d, J=8.0 Hz), 8.95(1H, br s), 9.50(1H, br s)

Example 39

N-(5,11-Dihydro-8-fluoro-2-hydroxydibenz(b,e)(1,4)oxazepin -6-yl)-4-methoxybenzenesulfonamide

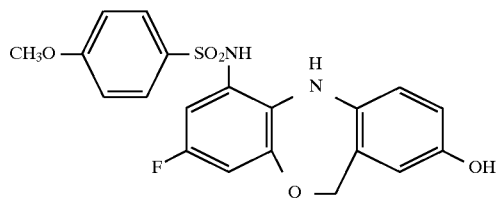

The title compound was obtained by a method similar to the one described in Example 30.

M.p.: 201° to 210° C. (gradually melting).

$^1$H-MMR(DMSO-d$_6$) δ(ppm): 3.70(3H, s), 4.80(2H, s), 6.35(1H, dd, J=9.6, 2.8 Hz), 6.50(1H, s), 6.59(2H, s), 6.68(1H, dd, J=9.6, 2.8 Hz), 6.85(1H, br), 6.96(2H, d, J=8.8 Hz), 7.56(2H, d, J=8.8 Hz), 8.96(1H, br s), 9.60(1H, br s)

Example 40

N-(5,11-Dihydrodibenz(b,e)(1,4)oxazepin-4-yl)-4-methoxybenzenesulfonamide

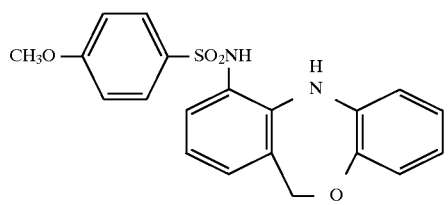

The title compound was obtained by a method similar to the one described in Example 1.

M.p.: 164.5°–166.5° C.

$^1$H-MMR(DMSO-d$_6$) δ(ppm): 3.66(3H, s), 4.90(2H, s), 6.63(1H, td, Jt=7.2, Jd=1.2 Hz), 6.66(1H, t, J=7.6 Hz), 6.74–6.89(6H, m), 7.04(1H, d, J=7.6 Hz), 7.28(1H, br s), 7.50(2H, d, J=8.8 Hz), 9.49(1H, br s)

Example 41

N-(10,11-Dihydro-10-ethyl-5H-dibenzo(b,e)(1,4)diazepin-6-yl)-4-methoxybenzenesulfonamide

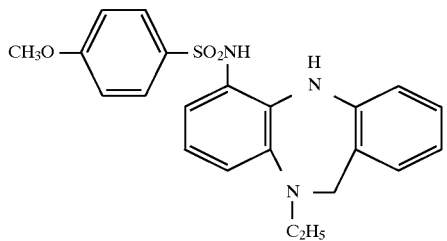

The title compound was obtained by reducing the compound of Example 37 with lithium aluminum hydride in accordance with a conventional method.

$^1$H-MMR(CDCl$_3$) δ(ppm): 1.14(3H, t, J=7.2 Hz), 3.03 (2H, q, J=7.2 Hz), 3.80(3H, s), 4.10(2H, s), 6.13(1H, br s), 6.18(1H, dd, J=8.0, 1.6 Hz), 6.44(1H, t, J=8.0 Hz), 6.72–6.76(2H, m), 6.82(1H, dd, J=8.0, 1.6 Hz), 6.88(2H, d, J=9.2 Hz), 6.97(1H, d, J=7.6 Hz), 7.11(1H, td, J=7.6, 1.6 Hz), 7.20(1H, br s), 7.68(2H, d, J=9.2 Hz)

Example 42

N-(5,11-Dihydro-2-hydroxydibenz(b,e)(1,4)oxazepin-6-yl)-5-methyl-2-thiophenesulfonamide

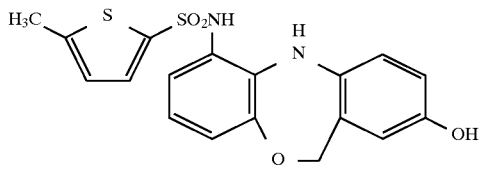

The title compound was obtained by a method similar to the one described in Example 30.

M.p.: 184°–188° C. (gradually melting).

$^1$H-MMR(DMSO-d$_6$) δ(ppm): 2.32(3H, s), 4.82(2H, s), 6.46–6.54(2H, m), 6.58(1H, d, J=7.6 Hz), 6.60–6.66(2H, m), 6.71(1H, d, J=3.6 Hz), 6.74(1H, br), 7.00(1H, br), 7.15(1H, d, J=3.6 Hz), 8.94(1H, br s), 9.69(1H, br s)

Example 43

N-(2-Aceltylamino-10,11-dihydro-5H-dibenzo(b,e)(1,4)diazepin-6-yl)-4-methoxybenzenesulfonamide

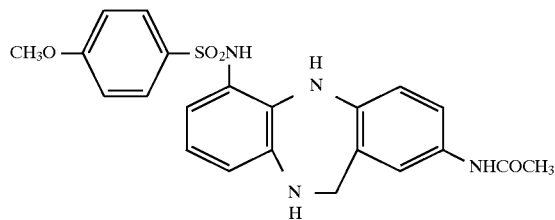

The title compound was obtained by a method similar to the one described in Example 31.

$^1$H-MMR(DMSO-d$_6$) δ(ppm): 1.98(3H, s), 3.72(3H, s), 3.94(2H, br d, J=2.8 Hz), 5.71(1H, br s), 6.14(1H, dd, J=8.0, 1.2 Hz), 6.36(1H, t, J=8.0 Hz), 6.56(1H, dd, J=8.0, 1.2 Hz), 6.59(1H, d, J=8.4 Hz), 6.95(2H, d, J=8.8 Hz), 6.98(1H, br s), 7.18(1H, d, J=2.4 Hz), 7.21(1H, dd, J=8.4, 2.4 Hz), 7.56(2H, d, J=8.8 Hz), 9.37(1H, br s), 9.67(1H, br s)

Example 44

N-(10,11-Dihydro-2-(3-hydroxypropyloxy)-5H-dibenzo(b,e)(1,4)diazepin-6-yl)-4-methoxybenzenesulfonamide

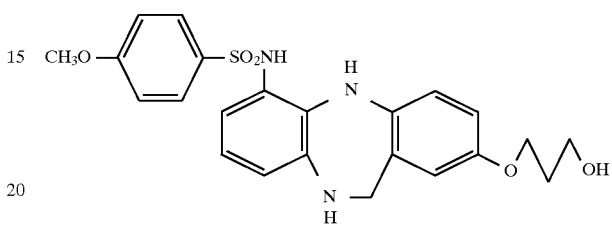

The title compound was obtained by a method similar to the one described in Example 31.

$^1$H-MMR(DMSO-d$_6$) δ(ppm): 1.79–1.85(2H, m), 3.54 (2H, dt, J=6.4, 5.2 Hz), 3.73(3H, s), 3.95(2H, t, J=6.4 Hz), 3.99(2H, br d, J=2.8 Hz), 4.53(1H, t, J=5.2 Hz), 5.68(1H, br s), 6.09(1H, dd, J=8.0, 1.2 Hz), 6.33(1H, t, J=8.0 Hz), 6.53(1H, dd, J=8.0, 1.2 Hz), 6.59(1H, d, J=8.8 Hz), 6.61(1H, d, J=3.2 Hz), 6.66 (1H, dd, J=8.8, 3.2 Hz), 6.82 (1H, br s), 6.97 (2H, d, J=8.8 Hz), 7.56(2H, d, J=8.8 Hz), 9.31(1H, br s)

Example 45

N-(5,11-Dihydro-2-fluoro-1-hydroxydibenz(b,e)(1,4)oxazepin-6-yl)-4-methoxybenzenesulfonamide

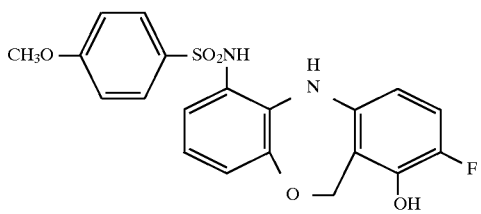

The title compound was obtained by a method similar to the one described in Example 30.

M.p.: 219°–232° C. (gradually melting).

$^1$H-MMR(DMSO-d$_6$) δ(ppm): 3.68(3H, s), 4.93(2H, s), 6.21(1H, dd, J=8.8, 4.0 Hz), 6.53(1H, dd, J=7.2, 2.4 Hz), 6.56(1H, t, J=7.2 Hz), 6.79(1H, dd, J=7.2, 2.4 Hz), 6.91(2H, d, J=8.8 Hz), 6.94(1H, dd, J=10.4, 8.8 Hz), 7.15(1H, br s), 7.50(2H, d, J=8.8 Hz), 9.45(1H, br s), 9.70(1H, br s)

Example 46

N-(4-Chloro-10,11-dihydro-2-fluoro-1-hydroxy-5H-dibenzo(b,e)(1,4)diazepin-6-yl)-4-methoxybenzenesulfonamide

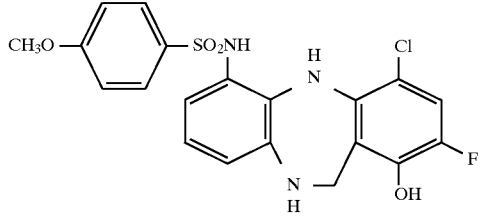

The title compound was obtained by a method similar to the one described in Example 31.

$^1$H-MMR(DMSO-d$_6$) δ(ppm): 3.81(3H, s), 4.20–4.22 (2H, m), 5.85(1H, br), 5.89(1H, br), 6.37(1H, br t, J=7.6 Hz), 6.58(1H, br), 7.07(2H, d, J=8.8 Hz), 7.25(1H, d, J=10.0 Hz), 7.63(1H, br), 7.64(2H, d, J=8.8 Hz), 9.43(1H, br s), 9.79(1H, br s)

Example 47

N-(10,11-Dihydro-2-fluoro-1-hydroxy-5H-dibenzo(b,e)(1,4)diazepin-6-yl)-4-methoxybenzenesulfonamide

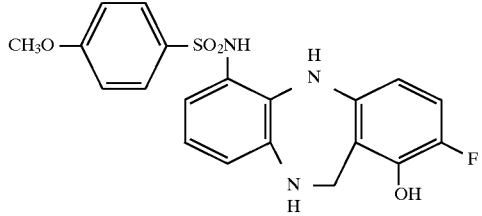

The compound of Example 46 was hydrogenated in the presence of palladium-carbon at room temperature under atmospheric pressure. After purifying by silica gel column chromatography and recrystallizing from chloroform-isopropyl ether, the title compound was obtained.

M.p.: 190°–192° C. (decomp.).

$^1$H-MMR(DMSO-d$_6$) δ(ppm): 3.72(3H, s), 4.06–4.08 (2H, m), 5.65(1H, br), 6.11–6.16(2H, m), 6.38(1H, t, J=7.6 Hz), 6.54(1H, brd, J=7.6 Hz), 6.84(1H, dd, J=10.4, 8.8 Hz), 6.90(1H, br s), 6.93(2H, d, J=8.8 Hz), 7.53(2H, d, J=8.8 Hz), 9.32(1H, br s), 9.39(1H, br s)

Example 48

N-(2-Cyano-10,11-dihydro-5H-dibenzo(b,e)1,4-diazepin-6-yl)-4-methoxybenzenesulfonamide

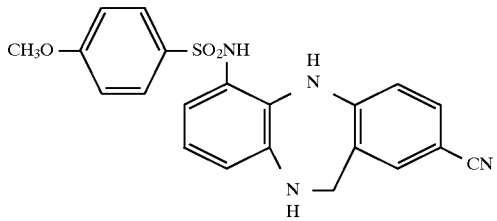

The title compound was obtained by a method similar to the one described in Example 31.

M.p.: 105°–107° C.

$^1$H-MMR(DMSO-d$_6$) δ(ppm) 3.64(3H, s), 3.40(2H, br d, J=2.8 Hz), 5.93(1H, br s), 6.42(1H, dd, J=8.0, 1.6 Hz), 6.57(1H, t, J=8.0 Hz), 6.68(1H, br), 6.76(1H, d, J=8.4 Hz), 6.85(2H, d, J=8.8 Hz), 7.38(1H, d, J=2.0 Hz), 7.41(1H, dd, J=8.4, 2.0 Hz), 7.48(2H, d, J=8.8 Hz), 7.7.6(1H, br s), 9.39(1H, br s)

Example 49

N-(10,11-Dihydro-8-fluoro-5H-dibenzo(b,e)(1,4)diazepin-4-yl)-4-methoxybenzenesulfonamide

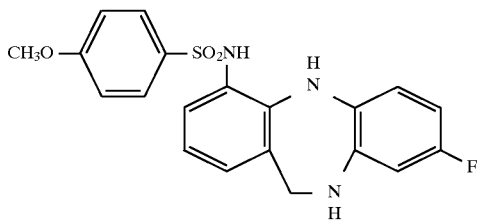

Starting with N-(2-((2-amino-4-fluorophenyl)amino)phenyl)-4-methoxybenzenesulfonamide, the title compound was obtained by a method similar to the one described in Example 31.

$^1$H-MMR(DMSO-d$_6$) δ(ppm): 3.71(3H, s), 4.09(2H, br d, J=3.6 Hz), 5.87(1H, br t, J=3.6 Hz), 6.29–6.41(2H, m), 6.50(1H, dd, J=8.4, 6.4 Hz), 6.53(1H, t, J=8.0 Hz), 6.69(1H, dd, J=8.0, 1.6 Hz), 6.87(1H, br s), 6.90(1H, br s), 6.91(2H, d, J=9.2 Hz), 7.51(2H, d, J=9.2 Hz), 9.42(1H, br s)

We claim:

1. A compound represented by the following formula (I) or a pharmacologically acceptable salt thereof:

wherein

G represents an aromatic 5- or 6-membered ring having 1 or 2 substituents, said substituents each being selected from the group consisting of a halogen atom, a linear or branched $C_1$–$C_6$ alkyl group, a linear or branched $C_1$–$C_6$ alkoxy group, and an amino group optionally substituted by linear or branched $C_1$–$C_6$ alkyl groups;

L represents oxygen or —N(R$^1$)—, wherein R$^1$ represents hydrogen or lower alkyl; and M represents

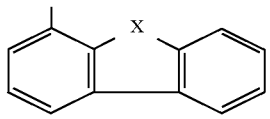

which fused phenyl rings can be optionally substituted with one or more substituents selected from the group consisting of a halogen atom, a linear or branched $C_1$–$C_6$ alkyl group optionally substituted by a hydroxy group, a linear or branched $C_1$–$C_6$ alkoxy group optionally substituted by a hydroxy group, a hydroxy group, an amino group optionally substituted by linear or branched $C_1$–$C_6$ alkyl groups optionally having a hydroxy group, $C_1$–$C_4$ acyl groups, a cyano group and an oxo group; and X represents —N($R^2$)—, wherein $R^2$ represents hydrogen or lower alkyl, or —NHCO— provided that a combination wherein G is 4-methylphenyl or 4-methoxycarbonylaminophenyl, and X is —N($R^2$)— is excluded therefrom.

2. The compound or a pharmacologically acceptable salt thereof as set forth in claim 1 wherein G is lower alkoxyphenyl.

3. The compound or a pharmacologically acceptable salt as set forth in claim 1 wherein L is NH.

4. The compound or a pharmacologically acceptable salt thereof as set forth in claim 1 wherein G is 4-methoxyphenyl.

5. A process for producing a compound or a pharmaceologically acceptable salt thereof as set forth in claim 1 comprising reacting a sulfonic acid represented by the following general formula (II):

Gb—SO₃H  (II)

wherein

Gb represents optionally protected G as defined in claim 1; or a reactive derivative thereof with a compound represented by the following general formula (III):

H—L—Ma  (III)

wherein

L has the same meaning as the one defined in claim 1; and

Ma represents optionally protected M as defined in claim 1;

and optionally removing the protecting group(s) of G, if any, of the product thus obtained.

6. A medicinal composition comprising an effective antitumor amount of a compound as set forth in claim 1, and a pharmacologically acceptable filler.

7. A method of treating nasopharyngeal cancer, pulmonary cancer, intestinal cancer, mammary cancer, uterus cancer, gastric cancer, ovarian cancer and liver cancer, comprising:

administering to a patient in need thereof, an effective anti-tumor amount of a compound or a pharmacologically acceptable salt thereof as set forth in claim 1.

8. A compound as set forth in claim 1, wherein G represents

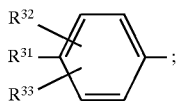

$R^{31}$ represents hydrogen, halogen, lower alkyl, lower alkoxy, nitro, cyano or amino optionally substituted by lower alkyl;

$R^{32}$ and $R^{33}$ are the same or different from each other and each represents hydrogen, lower alkyl, lower alkoxy or halogen.

* * * * *

UNITED STATES PATENT AND TRADEMARK OFFICE
CERTIFICATE OF CORRECTION

PATENT NO.    : 5,854,274
DATED         : December 29, 1998
INVENTOR(S)   : Yoshino et al.

It is certified that error appears in the above-identified patent and that said Letters Patent is hereby corrected as shown below:

Title page,
Item [22], Related U.S. Application Data, change "Division of Ser. No. 397,254, Mar. 23, 1995." to -- Division of Ser. No. 397,254, Mar. 23, 1995, which is a Continuation PCT/JP94/01231, July 26, 1994 published as WO95/03279, Feb. 2, 1995. --

Signed and Sealed this

Seventeenth Day of August, 2004

JON W. DUDAS
*Acting Director of the United States Patent and Trademark Office*